(12) United States Patent
Brophy et al.

(10) Patent No.: US 8,765,673 B2
(45) Date of Patent: *Jul. 1, 2014

(54) METHODS FOR PROMOTING WOUND HEALING AND/OR REDUCING SCAR FORMATION

(75) Inventors: Colleen Brophy, Scottsdale, AZ (US); Alyssa Panitch, Higley, AZ (US); Catherine Parmiter, Phoenix, AZ (US); Elizabeth Furnish, Tempe, AZ (US); Padmini Komalavilas, Tempe, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/343,127

(22) Filed: Jan. 4, 2012

(65) Prior Publication Data

US 2012/0238508 A1 Sep. 20, 2012

Related U.S. Application Data

(63) Continuation of application No. 10/545,518, filed as application No. PCT/US2004/004999 on Feb. 20, 2004, now Pat. No. 8,101,572.

(60) Provisional application No. 60/448,954, filed on Feb. 21, 2003, provisional application No. 60/512,211, filed on Oct. 17, 2003, provisional application No. 60/530,306, filed on Dec. 16, 2003.

(51) Int. Cl.
*A61P 17/02* (2006.01)
*A61P 17/00* (2006.01)
*A61K 38/02* (2006.01)
*A61K 38/16* (2006.01)

(52) U.S. Cl.
USPC ......... 514/9.4; 514/18.6; 514/21.3; 514/21.4; 530/324; 530/325; 530/340

(58) Field of Classification Search
None
See application file for complete search history.

(56) References Cited

U.S. PATENT DOCUMENTS

| | | | |
|---|---|---|---|
| 5,710,172 A | 1/1998 | Kukreja et al. |
| 5,985,635 A | 11/1999 | Bandman et al. |
| 6,475,490 B1 | 11/2002 | Srivastava et al. |
| 7,135,453 B2 | 11/2006 | Brophy et al. |
| 7,381,699 B2 | 6/2008 | Brophy et al. |
| 2003/0060399 A1 | 3/2003 | Brophy et al. |
| 2003/0190364 A1 | 10/2003 | Panitch et al. |
| 2004/0192592 A1 | 9/2004 | Weiner et al. |
| 2008/0132443 A1 | 6/2008 | Brophy et al. |
| 2009/0176694 A1 | 7/2009 | Brophy et al. |
| 2009/0176695 A1 | 7/2009 | Brophy et al. |
| 2009/0258819 A1 | 10/2009 | Brophy et al. |
| 2010/0009903 A1 | 1/2010 | Brophy et al. |

FOREIGN PATENT DOCUMENTS

| | | |
|---|---|---|
| JP | 2001/278894 A | 10/2001 |
| WO | WO-01/98497 A1 | 12/2001 |
| WO | WO-03/018758 A2 | 3/2003 |
| WO | WO-2004/017912 A2 | 3/2004 |
| WO | WO-2004/075914 A1 | 9/2004 |
| WO | WO-2005/037236 | 4/2005 |

OTHER PUBLICATIONS

Nicolaou et al., J. Biol. Chem., 2008, vol. 283(48):33465-33471.*
Velnar et al., J. Int'l Med. Res., 2009, vol. 37:1528-1542.*
Akamatsu, et al., "Potent Inhibition of Protein-Tyrosine Phosphatase by Phosphotyrosine-Mimic Containing Cyclic Peptides", 1997, Bioorg. Med. Chem., vol. 5 (1), pp. 157-163.
Anderson, et al., "Cyclic GMP-Dependent Protein Kinase Expression in Coronary Arterial Smooth Muscle in Response to Balloon Catheter Injury", 2000, Arterioscler. Thromb. Vasc. Biol., vol. 20, pp. 2191-2197.
Beall, et al., "Cyclic Nucleotide-Dependent Vasorelaxation is Associated with the Phosphorylation of a Small Heat Shock-Related Protein", 1997, J. Biol. Chem., vol. 272, pp. 11283-11297.
Beall, et al., "The Small Heat Shock-related Protein, HSP20, is Phosphorylated on Serine 16 during Cyclic Nucleotide-dependent Relaxation", 1999, J. Biol. Chem., vol. 274, pp. 11344-11351.
Beall, et al., Additions and Corrections to the Journal of Biological Chemistry, The small heat shock related protein, HSP20, is phosphorylated on serin1 16 during cyclic nucleotide-dependent relaxation, 1999, 274(16), 11344-11351, p. 28058.
Bergh, et al., "Impaired cyclic nucleotide-dependent vasorelaxation in human umbilical artery smooth muscle", 1995, The American Physiological Society, vol. 268, pp. H202-H212.
Bertling, et al., "Cyclase-associated Protein 1 (CAP1) Promotes Cofilin-induced Actin Dynamics in Mammalian Nonmuscle Cells", 2004, Mol. Biol. Cell, vol. 15, pp. 2324-2334.
Birkenfeld, et al., "Identification of Cofilin and LIM-domain-containing Protein Kinase 1 as Novel Interaction Partners of 14-3-3. zeta.", 2003, Biochem J., vol. 369, pp. 45-54.
Boerth, et al., "Cyclic GMP-Dependent Protein Kinase Regulates Vascular Smooth Muscle Cell Phenotype", 1997, J. Vasc. Res., vol. 34, p. 245-259.
Brophy, et al., "Small Heat Shock Proteins and Vasospasm in Human Umbilical Artery Smooth Muscle", 1997, Biology of Reproduction, 57(6): pp. 1354-1359.
Brophy, et al., "Cellular mechanisms of cyclic nucleotide-induced vasorelaxation", 1997, Journal of Vascular Surgery, vol. 25, (2), 8 pp.
Brophy, et al., "Regulation of Vasomotor Tone and Vasospasm", 1997, The Basic Science of Vascular Disease, Chapter 13, pp. 367-384.
Brophy, et al., "Heat shock protein expression in umbilical artery smooth muscle", 1998, Journal of Reproduction and Fertility, vol. 114, pp. 351-355.

(Continued)

*Primary Examiner* — Xiaozhen Xie
(74) *Attorney, Agent, or Firm* — McCarter & English, LLP; Steven G. Davis

(57) ABSTRACT

The present invention provides methods for promoting wound healing and/or reducing scar formation, by administering to an individual in need thereof one or more of the heat shock protein 20-derived polypeptides disclosed herein.

9 Claims, 2 Drawing Sheets

(56) References Cited

OTHER PUBLICATIONS

Brophy, et al., "The small heat shock-related protein-20 is an actin-associated protein", 1999, Journal of Vascular Surgery, vol. 29 (2), pp. 326-333.
Brophy, et al., "Phosphorylation of the Small Heat Schok-Related Protein, HSP20, in Vascular Smooth Muscles is Associated with Changes in the Macromolecular Associations of HSP20", 1999, J. Biol. Chem., vol. 274, pp. 6324-6329.
Brophy, et al., "The small heat shock-related protein-20 is an actin-associated protein", 1999, Journal of Vascular Surgery: Official Publication, The Society for Cardiovascular Surgery, North American Chapter, vol. 29 (2), pp. 326-333.
Brophy, et al., "Functional Expression of NOS 1 in Vascular Smooth Muscle", 2000, Am. J. Physiol. Heart Circ. Physiol., vol. 278, pp. H991-H997.
Brophy, et al., "The macromolecular associations of heat shock protein-27 in vascular smooth muscle", 2000, Surgery, vol. 128 (2), pp. 320-326.
Carpino, et al., "The 9-Fluorencylmethoxycarbonyl Amino-Protecting Group", 1972, J. Org. Chem., vol. 37, pp. 3404-3409.
Co-Pending U.S. Appl. No. 11/078,256, filed Mar. 11, 2005, Brophy, et al.
Database WPI Week 200212, Thomson Scientific, London, GB, AN2002-085935.
Elbert, et al., "Cofilin Peptide Homologs Interfere with Immunological Synapse Formation and T Cell Activation", 2004, PNAS, vol. 101, pp. 1957-1962.
Examination Report for European Application No. 02759442.3 dated Jan. 15, 2007.
Examination Report in European Patent App. No. 06014290.8, dated Mar. 10, 2008.
Fawell, et al., "Tat-mediated Delivery of Heterologous Proteins into Cells", 1994, PNAS, vol. 91, pp. 664-668.
Flynn, et al., "Transduction of biologically active motifs of the small heat shock-related protein HSP20 leads to relaxation of vascular smooth muscle", 2003, The Faseb Journal, vol. 17, pp. 1358-1360.
Frankel, et al., "Cellular Uptake of the Tat Protein from Human Immunodeficiency Virus", 1988, Cell, vol. 55, pp. 1189-1193.
Fu, et al., "14-3-4 Proteins: Structure, Function, and Regulation", 2000, Annu. Rev. Pharmacol. Toxicol., vol. 40, pp. 617-647.
Fuchs, et al., "Stress causes decrease in vascular relaxation linked with altered phosphorylation of heat shock proteins", 2000, Am. J. Physiol. Regulatory Integrative Comp. Physiol., vol. 279, pp. R492-R498.
Ghosh, et al., "Cofilin Promotes Actin Polymeriation and Defines the Direction of Cell Motility", 2004, Science, vol. 304, pp. 743-746.
Gohla, et al., "14-3-3 Regulates Actin Dynamics by Stabilizing Phosphorylated Cofilin", 2002, Current Biology, vol. 12, pp. 1704-1710.
Green, et al., "Autonomous Functional Domains of Chemically Synthesized Human Immunodeficiency Virus Tat Trans-Activator Protein", 1988, Cell, vol. 55, pp. 179-1188.
Heacock, et al., "The Quantitation of G- and F-Actin in Cultured Cells", 1983, Anal. Biochem., vol. 135, pp. 22-36.
Hedges, et al., "A Role for p38.sup.MAPK/HSP27 Pathway in Smooth Muscle Cell Migration", 1999, The Journal of Biological Chemistry, vol. 274 (34), pp. 24211-24219.
Ho, et al., "Synthetic Protein Transduction Domains: Enhanced Transduction Potential in Vitro and in Vivo", 2001, Cancer Res, vol. 61, pp. 474-477.
Inaguma, et al., "cDNA cloning of a 20-kDa protein (p20) highly homologous to small heat shock proteins: developmental and physiological changes in rat hindlimb muscles", 1996, Gene, vol. 178, pp. 145-150.
International Search Report and Written Opinion—(PCT/US2004/034989) Date of Mailing Oct. 19, 2005.
International Search Report and Written Opinion—(PCT/US2004/004999) Date of Mailing Jul. 22, 2004.
Jerius, et al., "Endothelial-dependent vasodilation is associated with increases in the phosphorylation of a small heat shock protein (HSP20)", 1999, J. Vasc. Surg., vol. 29, pp. 678-684.
Kato, et al., "Purification and Characterization of a 20-kDa Protein That is Highly Homologous to a Crystallin", 1994, J. Biol. Chem., vol. 269, pp. 15302-15309.
Knoepp, et al., "Cellular Stress Inhibits Vascular Smooth Muscle Relaxation", 1999, J. Vasc. Surg., vol. 31, pp. 343-353.
Knoepp, et al., "Cellular stress inhibits smooth muscle relaxation", 1999, Surgical Forum, vol. 50, pp. 432-434.
Dreiza, et al., "Transducible Heat Shock Protein 20 (HSP20) phosphopeptide Alters Cytoskeletal Dynamics", FASEB J. express article 10.1096/fj.04-2911fje. Published online Dec. 14, 2004.
Komalavilas, et al., "PI3-kinase/Akt modulates vascular smooth muscle tone via cAMP signaling pathways", 2001, J. Appl. Physiol., vol. 91, pp. 1819-1827.
Lavoie, et al., "Modulation of Cellular Thermoresistance and Actin Filament Stability Accompanies Phosphorylation-Induced Changes in the Oligomeric Structure of Heat Shock Protein 27", 1995, Molecular and Cellular Biology, vol. 15 (1), pp. 505-516.
Macomson, et al., "Heat Shock Protein Expression in Cerebral Vessels After Subarachnoid Hemorrhage", 2002, Neurosurgery, vol. 51, p. 204.
Matsuno, et al., "A heat shock-related protein, p20, plays and inhibitory role in platelet activation", 1998, FEBS Letters, vol. 429, pp. 327-329.
Merrifield, R.B., "Solid Phase Peptide Synthesis. I. The Synthesis of a Tetrapeptide", 1963, J. Am. Chem. Soc., vol. 85, pp. 2149-2154.
Morris, et al., "An Essential Phosphorylation-site Domain of Human cdc25C Interacts with Both 14-3-3 and Cyclins", 2000, J. Biol. Chem., vol. 275, pp. 28849-28857.
Murphy-Ullrich, et al., "Heparin-binding Peptides from Thrombospondins 1 and 2 Contain Focal Adhesion-labilizing Activity", 1993, J. Biol. Chem., vol. 268 (35), pp. 26784-26789.
Murphy-Ullrich, et al., "Cyclic GMP-dependent protein kinase is required for thrombospondin and tenascin mediated focal adhesion disassembly", 1996, J. Cell. Sci., vol. 109, p. 2499-2508.
Niwa, et al., "Small Molecular Weight Heat Shock-related Protein, HSP20, Exhibits and Anti-Platelet Activity by Inhibiting Receptor-Mediated Calcium Influx", 2000, Elsevier Life Sciences, vol. 66 (1), pp. PL7-PL12.
Niwa, et al., "Control of Actin Reorganization by Slingshot, a Family of Phosphatases that Dephosphorylate ADF/Cofilin", 2002, Cell, vol. 108, pp. 233-246.
O'Connor, et al., "Heat-induced force suppression and HSP20 Phosphorylation in Swine carotid media", 2002, J. Appl. Physiol., vol. 93, pp. 484-488.
Otaka, et al., "Synthesis and Application of N-Boc-L-2-amino-4(diethylphosphono)-4,4-difluorobutanoic acid for Solid-Phase Synthesis of Nonhydrolyzable Phosphoserine Peptide Analogues", 1995, Pergamon, Tetrahedron Letters, Elsevier Science Ltd., vol. 36 (6), pp. 927-930.
Paavilainen, et al., "Structural Conservation between the Actin Monomer-binding Sites of Twinfilin and Actin-depolymerizing Factor (ADF)/Cofilin", 2002, J. Biol. Chem., vol. 277, pp. 43089-43095.
Parmiter, et al., "Protein transduction of biomimetic peptides leads to changes in the actin cytoskeleton of 3T3 cells", 2003, FASEB Journal, vol. 17 (4-5), Abstract No. 599.6.
Pfannstiel, et al., "Human Cofilin Forms Oligomers Exhibiting Actin Bundling Activity", 2001, J. Biol. Chem., vol. 276, pp. 49476-49484.
Ramakers, et al. "Regulation of Astrocycle Morphology by RhoA and Lysophosphatidic Acid", 1998, Exp. Cell Res., vol. 245, pp. 252-262.
Rembold, et al., "Caldesmon and heat shock protein 20 phosphorylation in nitroglycerin and magnesium-induced relaxation of swine carotid artery", 2000, Elsevier Biochimica et Biophysica Acta, vol. 1500, pp. 257-264.
Rembold, et al., "cGMP-mediated phosphorylation of hat shock protein 20 may cause smooth muscle relaxation without mysin light chain dephosphorylation in swine carotid artery", 2000, Journal of Physiology, vol. 524 (3), 865-878.
Rembold, et al., "Localization of heat shock protein 20 in swine carotid artery", 2001, BMC Physiology, vol. 1, pp. 1-7.

(56) References Cited

OTHER PUBLICATIONS

Rembold, et al., "Singal Transduction in Smooth Muscle, Selected Contribution: HSP20 Phosphorylation in Nitroglycerin- and Forskolin-Induced Sustained Reductions in Swine Carotid Media Tone", 2001, J. Appl. Physiol., vol. 91, pp. 1460-1466.

Rembold, et al., "Letters to the Editor", 2002, J. Appl. Physiol., vol. 92, pp. 890-891.

Schwarze, et al., "In Vivo Protein Transduction: Delivery of a Biologically Active Protein into the Mouse", 1999, Science, vol. 285, pp. 1569-1572.

Shen, et al., "Significance of 14-3-3 Self-Dimerization for Phosphorylation-dependent Target Binding", 2003, Mol. Biol. Cell., vol. 14, pp. 4721-4733.

Supplemental European Search Report for EP App. No. 06014290.8, dated Sep. 24, 2007.

Supplemental European Search Report for EP Application No. 02759442.3, dated Apr. 27, 2006.

Supplementary European Search Report—EP04796051, Date of Completion of the Search Jun. 26, 2009.

Tessier, et al., "The Small Heat Shock Protein (HSP) 20 is Dynamically Associated with the Actin Cross-Linking Protein Actinin", 2003, J. Surg. Res., vol. 111 (1) pp. 152-157.

Tyagi, et al., "Internalization of HIV-1 Tat Requires Cell Surface Heparan Sulfate Proteoglycans", 2001, J. Biol. Chem., vol. 276, pp. 3254-3261.

U.S. Non-Final Office Action for U.S. Appl. No. 10/575,294, issued on Sep. 24, 2010.

Van de Klundert, et al., "The mammalian small heat-shock protein Hsp20 forms dimmers and is a poor chaperone", 1998, Eur. J. Biochem., vol. 258 (3), 8 pp.

Wadia, et al., "Protein transduction technology", 2002, Curr. Opin. Biotechnol., vol. 13, pp. 52-56.

Wang, et al., "Phosphorylation of P20 is associated with the actions of insulin in rat skeletal and smooth muscle", 1999, Biochem. J., vol. 344, pp. 971-976.

Wang, et al., "Alteration in Phosphorylation of P20 is Associated with Insulin Resistance", 2001, Diabetes, vol. 50, pp. 1821-1827.

Washburn, et al., "Large-scale Analysis of the Yeast Proteome by Multidimensional protein Identification Technology", 2001, Nat. Biotechnol., vol. 19, pp. 242-247.

Wilker, et al., "14-3-3 Proteins—a Focus on Cancer and Human Disease", 2004, J. Mol. Cell Cardiol., vol. 37, pp. 633-642.

Woodrum, D., "The Role of the Small Heat ShockProteins, HSP20 and HSP27 in Cyclic Nucleotide Dependent Vasorelaxation", 1999, Dissertation submitted to the Faculty of the School of Graduate Studies of the Medical College of Georgia in partial fulfillment of the requirements of the degree of Doctor of Philosphy, pp. 1-136.

Woodrum, et al., "Phosphorylation events associated with cyclic nucleotide-dependent inhibition of smooth muscle contraction", 1999, Am. J. Physiol., pp. H931-H939.

Woodrum, et al., "The paradox of smooth muscle physiology", 2001, Elsevier, Molecular and Cellular Endocrinology, vol. 177, pp. 135-143.

Yaffe, et al., "The Structural Basis for 14-3-3:Phosphopeptide Binding Specificity", 1997, Cell, vol. 91, pp. 961-971.

Yamboliev, et al., "Evidence for Modulation of Smooth Muscle Force by the p38 MAP kinase/HSP27 pathway", 2000, Am. J. Physiol. Heart Circ. Physiol., vol. 278, pp. H1899-H1907.

Zhang, et al., "Serine Phosphorylation-dependent Association of the Band 4.1-related Protein-tyrosine Phosphatase PTPH1 with 14-3-3. beta. Protein", 1997, J. Biol. Chem., vol. 272, pp. 27281-27287.

* cited by examiner

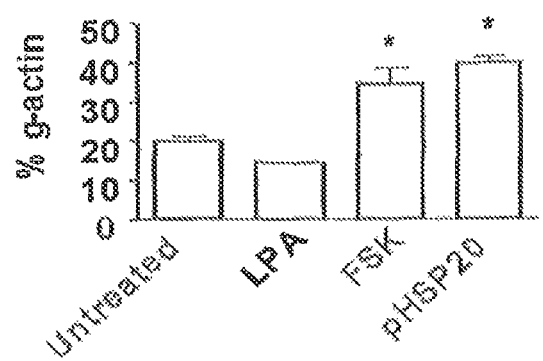
Figure 1: PhosphoHSP20 peptide disrupts the actin cytoskeleton.

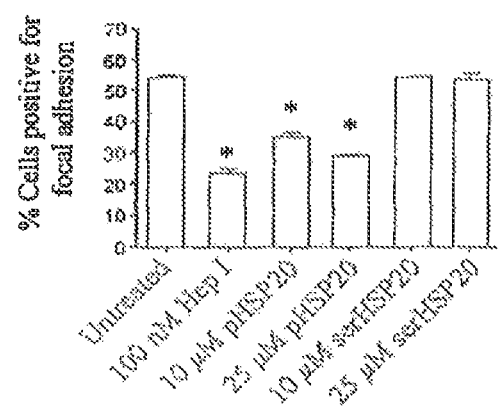
Figure 2: PhosphoHSP20 peptide disrupts focal adhesions.

025
METHODS FOR PROMOTING WOUND HEALING AND/OR REDUCING SCAR FORMATION

CROSS REFERENCE

This application is a continuation of U.S. patent application Ser. No. 10/545,518 filed, Sep. 30, 2009, now U.S. Pat. No. 8,101,572, which is a 371 National Stage Application of PCT/US2004/004999, filed Feb. 20, 2004, which claims priority to U.S. Provisional Patent Application Serial Nos. 60/448,954 filed Feb. 21, 2003; 60/512,211 filed Oct. 17, 2003; and 60/530,306 filed Dec. 16, 2003, each of which is incorporated by reference herein in its entirety.

STATEMENT OF GOVERNMENT RIGHTS

This work was supported by a VA Merit Review Award and NIH RO1 HL58027-01.

FIELD OF INVENTION

This invention relates generally to methods for promoting wound healing and inhibiting scar formation.

BACKGROUND OF THE INVENTION

The primary goal in the treatment of wounds is to achieve wound closure. Many wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Thus, therapeutics that provide a benefit to any of these components provide a benefit to the wound healing process.

During wound healing, cells, including fibroblasts, migrate into the wound area. These cells form stress fibers and focal adhesions that serve to help close the wound during the wound contraction step. While wound contraction is an essential component of wound healing, the development of scar contractures in tissues and organs disrupts normal organ integrity and produces functional deformities. Limiting wound contraction during the wound healing process allows the surrounding tissue more time to regenerate and heal with reduced scarring. Thus, compounds that limit wound contraction can be used to reduce scar formation that accompanies wound healing.

It has recently been determined that cyclic nucleotide-dependent relaxation of vascular smooth muscle is associated with an increase in the phosphorylation of the small heat shock related protein 20 ("HSP20"). HSP20 is highly and constitutively expressed in muscle tissues and can be phosphorylated in vitro by cGMP-dependent protein kinase. HSP20 has been shown to associate with actin and $\alpha$-actinin, a focal adhesion protein. Activation of cyclic nucleotide dependent signaling pathways also leads to a decrease in the association of HSP20 with $\alpha$-actinin, suggesting that HSP20 may lead to relaxation of vascular smooth muscle through a dynamic association with cytoskeletal proteins.

However, the role of HSP20 and peptides derived therefrom in modulation of wound healing and scar formation responses is not known.

SUMMARY OF THE INVENTION

The present invention provides methods to promote wound healing and/or reduce scar formation, comprising administering to an individual in need thereof an amount effective to promote wound healing and/or reduce scar formation of one or more polypeptides comprising a sequence according to general formula I:

X1-A(X2)APLP—X3 wherein X1 is 0-14 amino acids of the sequence of heat shock protein 20 between residues 1 and 14 of SEQ ID NO: 298;

X2 is selected from the group consisting of S, T, Y, D, E, hydroxylysine, hydroxyproline, phosphoserine analogs, and phosphotyrosine analogs; and X3 is selected from the group consisting of (a) 0-140 amino acids of heat shock protein 20 between residues 21 and 160 of SEQ ID NO:298; and (b) 0, 1, 2, or 3 amino acids of a sequence of genus Z1-Z2-Z3, wherein Z1 is selected from the group consisting of G and D;

Z2 is selected from the group consisting of L and K; and

Z3 is selected from the group consisting of S, T, and K.

BRIEF DESCRIPTION OF THE DRAWINGS

FIG. 1: PhosphoHSP20 peptide disrupts the actin cytoskeleton. 3T3 cells were cultured and treated as indicated on the graph (4). Monomer g-actin was biochemically quantitated using a DNase 1 inhibition assay. The level of g-actin in the cell extract that caused 50% inhibition of DNase 1 was estimated from a standard actin curve that was determined using known amounts of actin, * P<0.05 compared to untreated cells.

FIG. 2: FITC-phosphoHSP20 peptide disrupts focal adhesions. Results from the focal adhesion assay using interference reflective microscopy on 3T3 cells treated as described (4). Each condition was tested in triplicate, and an average of 250 cells per coverslip was counted. A cell was scored positive if it contained at least five focal adhesions. Hep I (peptide from thrombospondin 1) was used as a positive control. * P<0.05 compared to untreated cells.

DETAILED DESCRIPTION OF THE INVENTION

All references cited are herein incorporated by reference in their entirety.

Within this application, unless otherwise stated, the techniques utilized may be found in any of several well-known references such as: *Molecular Cloning: A Laboratory Manual* (Sambrook, at al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

As used herein, the singular forms "a", "an" and "the" include plural referents unless the context clearly dictates otherwise. For example, reference to a "polypeptide" means one or more polypeptides.

In one aspect, the present invention provides methods for promoting wound healing and/or reducing scar formation comprising administering to an individual in need thereof an amount effective to promote wound healing and/or reduce scar formation of a polypeptide comprising or consisting of a sequence according general formula I:

X1-A(X2)APLP—X3 wherein X1 is 0-14 amino acids of the sequence of heat shock protein 20 between residues 1 and 14 of SEQ ID NO: 298;

X2 is selected from the group consisting of S, T, Y, D, E, hydroxylysine, hydroxyproline, phosphoscrine analogs, and phosphotyrosine analogs; and X3 is selected from the group consisting of (a) 0-140 amino acids of residues 21 and 160 of SEQ ID NO:298; and (b) 0, 1, 2, or 3 amino acids of a sequence of genus Z1-Z2-Z3, wherein Z1 is selected from the group consisting of G and D;

Z2 is selected from the group consisting of L and K; and

Z3 is selected from the group consisting of S, T, and K.

Residues 15-21 from HSP20, with possible substitutions at residue 16 of HSP20 form the structural core of the polypeptides according to general formula I (A(X2)APLP) (SEQ ID NO: 2). The full sequence of HSP20 is provided as SEQ ID NO: 298, and is shown below:

```
Met Glu Ile Pro Val Pro Val Gln Pro Ser Trp Leu Arg Arg Ala Ser Ala Pro Leu

Pro Gly Leu Ser Ala Pro Gly Arg Leu Phe Asp Gln Arg Phe Gly Glu Gly Leu Leu

Glu Ala Glu Leu Ala Ala Leu Cys Pro Thr Thr Leu Ala Pro Tyr Tyr Leu Arg Ala

Pro Ser Val Ala Leu Pro Val Ala Gln Val Pro Thr Asp Pro Gly His Phe Ser Val Leu

Leu Asp Val Lys His Phe Ser Pro Glu Glu Ile Ala Val Lys Val Val Gly Glu His Val

Glu Val His Ala Arg His Glu Glu Arg Pro Asp Glu His Gly Phe Val Ala Arg Glu

Phe His Arg Arg Tyr Arg Leu Pro Pro Gly Val Asp Pro Ala Ala Val Thr Ser Ala

Leu Ser Pro Glu Gly Val Leu Ser Ile Gln Ala Ala Pro Ala Ser Ala Gln Ala Pro Pro

Pro Ala Ala Ala Lys.
```

The underlined residues represent amino acids 15-21.

X1 is 0-14 amino acids of SEQ ID NO: 298 between residues 1 and 14 of SEQ ID NO:298 (shown in italics above). Thus, if X1 is 5 amino acids of residues 1 and 14 of SEQ ID NO:298, then X1 would be the 5 amino acids contiguous to residues 15-21, eg: SWLRR (SEQ NO:303). Similarly, where X1 is the following number of amino acids of residues 1-14 of SEQ ID NO:298, its identity is as shown below:

```
1 amino acid of SEQ ID NO: 298:    R 2 amino acids of SEQ ID NO: 298:   RR 3 amino acids of SEQ ID NO: 298:   LRR (SEQ ID NO: 304)

4 amino acids of SEQ ID NO: 298:   WLRR (SEQ ID NO: 1)

6 amino acids of SEQ ID NO: 298:   PSWLRR (SEQ ID NO: 305)

7 amino acids of SEQ ID NO: 298:   NPSWLRR (SEQ ID NO: 306)

8 amino acids of SEQ ID NO: 298:   VNPSWLRR (SEQ ID NO: 307)

9 amino acids of SEQ ID NO: 298:   PVNPSWLRR (SEQ ID NO: 308)

10 amino acids of SEQ ID NO: 298:  VPVNPSWLRR (SEQ ID NO: 309)

11 amino acids of SEQ ID NO: 298:  PVPVNPSWLRR (SEQ ID NO: 310)

12 amino acids of SEQ ID NO: 298:  IPVPPVNPSWLRR (SEQ ID NO: 311)

13 amino acids of SEQ ID NO: 298:  EIPVIPPVNPSWLRR (SEQ ID NO: 312)

14 amino acids of SEQ ID NO: 298:  MEIPVPPVNPSWLRR (SEQ ID NO: 313)
```

In a further embodiment, X1 is 0, 1, 2, 3, or 4 amino acids of the sequence WLRR (SEQ ID NO:1).

In one embodiment, X3 is 0-140 amino acids between residues 21 and 160 of SEQ ID NO:298. According to this embodiment, X3 can be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 120, 120, 121, 122, 123, 124, 125, 126, 127, 128, 129, 130, 131, 132, 133, 134, 135, 136, 137, 138, 139 or 140 amino acids between residues 21 and 160 of SEQ ID NO:298.

For example, if X3 is 5 amino acids between residues 21 and 160 of SEQ ID NO:298, then X3 would be the 5 amino acids contiguous to residues 15-21, eg: GLSAP (SEQ ID NO: 314). Other possible X3 sequences will be apparent to one of skill in the art based on the teachings provided herein.

In another embodiment, X3 is 0, 1, 2, or 3 amino acids of a sequence of genus Z1-Z2-Z3, wherein Z1 is selected from the group consisting of G and D;

Z2 is selected from the group consisting of L and K; and

Z3 is selected from the group consisting of S, T, and K.

For example, if X3 is 2 amino acids of a sequence of the genus Z1-Z2-Z3, then the possibilities for X3 are GL, GK, DL, and DK. Other possible X3 sequences in this embodiment will be apparent to one of skill in the art based on the teachings provided herein.

According to various embodiments of the polypeptides of general formula I, X2 is S, T, Y, D E, a phosphoserine mimic, or a phosphotyrosine mimic. It is preferred that X2 is S, T, or Y; more preferred that X2 is S or T, and most preferred that X2 is S. In these embodiments where X2 is S, T, or Y, it is most preferred that X2 is phosphorylated. When X2 is D or E, these residues have a negative charge that mimics the phosphorylated state. The polypeptides of general formula I are optimally effective in the methods of the invention when X2 is phosphorylated, is a phosphoserine or phosphotyrosine mimic, or is another mimic of a phosphorylated amino acid residue, such as a D or B residue. Examples of phosphoserine mimics include, but are not limited to, sulfoserine, amino acid mimics containing a methylene substitution for the phosphate oxygen, 4-phosphono(difluoromethyl)phenylanaline, and L-2-amino-4-(phosphono)-4,4-difluorobutanoic acid. Other phosphoserine mimics can be made by those of skill in the art. Examples of phosphotyrosine mimics include, but are not limited to, phosphonomethylphenylalanine, difluoro-phosphonomethylphenylalanine, fluoro-O-malonyltyrosine and O-malonyltyrosine.

In a preferred embodiment, the polypeptide according to the general formula comprises or consists of an amino acid sequence according to SEQ ID NO:300 (WLRRApSAP-LPGL), wherein the "pS" represents a phosphorylated serine residue.

In another embodiment, the polypeptides according to general formula I may further comprise one or more molecules comprising an aromatic ring. In one such embodiment, the one or molecules comprising an aromatic ring are amino acids, such as any combination of 1-5 phenylalanine (F), tyrosine (Y), or tryptophan (W) residues. Thus, for example, the polypeptides according to general formula I can further comprise any combination of F, Y, and W, such as F, FF, Y, YY, W, WW, FY, FW, YF, YW, WY, WF, or a 3, 4, or 5 amino acid combination of F, Y, and W. In another embodiment, the molecule comprising an aromatic ring is one or more molecules comprising one or more aromatic rings that can optionally be substituted with halogen, lower alkyl, lower alkylthio, trifluoromethyl, lower acyloxy, aryl, and heteroaryl. For example, the one or more molecules comprising one or more aromatic ring may comprise 9-fluorenylmethyl (Fm). Examples of such molecules include, but are not limited to 9-fluorenylmethylcarbonyl, 9-fluorenylmethylcarbamates, 9-fluorenylmethylcarbonates, 9-fluorenylmethyl esters, 9-fluorenylmethylphosphates, and S-9-fluorenylmethyl tioethers. In embodiments wherein the molecule comprising an aromatic ring is not an amino acid, it can be attached to the polypeptide by methods known in the art, including but not limited to, standard Fmoc protection chemistry employed in peptide synthesis.

Thus, according to these various embodiments, a representative sample of polypeptides according to general formula I for use in the methods of the invention include, but are not limited to, polypeptides comprising or consisting of the following sequences: (ASAPLP) (SEQ ID NO:3); (ATAPLP) (SEQ ID NO:4); (RASAPLP) (SEQ ID NO:5); (RATAPLP) (SEQ ID NO:6); (AYAPLP) (SEQ ID NO:7); (RAYAPLP) (SEQ ID NO:8); (RRASAPLP) (SEQ ID NO:9); (LR-RASAPLP) (SEQ ID NO:10); (WLRRASAPLP); (SEQ ID NO:11) (RRATAPLP) (SEQ ID NO:12); (LRRATAPLP) (SEQ ID NO:13); (WLRRATAPLP) (SEQ ID NO:14); (RRAYAPLP) (SEQ ID NO:15); (LRRAYAPLP) (SEQ ID NO:16); (WLRRAYAPLP) (SEQ ID NO:17); (RRASAP-LPG) (SEQ ID NO:18); (RRASAPLPD) (SEQ ID NO:19); (RRASAPLPGL) (SEQ ID NO:20); (RRASAPLPGK) (SEQ ID NO:21); (RRASAPLPDL) (SEQ ID NO:22); (RRASAP-LPDK) (SEQ ID NO:23); (RRASAPLPGLS) (SEQ ID NO:24); (RRASAPLPGLT) (SEQ ID NO:25); (RRASAP-LPGKS) (SEQ ID NO:26); (RRASAPLPGKT) (SEQ ID NO:27); (RRASAPLPDLS) (SEQ ID NO:28); RRASAPLP-DLT) (SEQ ID NO:29); (RRASAPLPDKS) (SEQ ID NO:30); (RRASAPLPDKT) (SEQ ID NO:31); (LRRASAP-LPG) (SEQ ID NO:32); (LRRSAPLPD) (SEQ ID NO:33); (LRRASAPLPGL) (SEQ ID NO:34); (LRRASAPLPGK) (SEQ ID NO:35); (LRRASAPLPDL) (SEQ ID NO:36); (LR-RASAPLPDK) (SEQ ID NO:37); (LRRASAPLPGLS) (SEQ ID NO:38); (LRRASAPLPGLT) (SEQ ID NO:39); (LR-RASAPLPGKS) (SEQ ID NO:40); (LRRASAPLPGKT) (SEQ ID NO:41); (LRRASAPLPDLS) (SEQ ID NO:42); (LRRASAPLPDLT) (SEQ ID NO:43); (LRRASAPLPDKS) (SEQ ID NO:44); (LRRASAPLPDKT) (SEQ ID NO:45); (WLRRASAPLPG) (SEQ ID NO:46); (WLRRASAPLPD) (SEQ ID NO:47); (WLRRASAPLPGL) (SEQ ID NO:48); (WLRRASAPLPGK) (SEQ ID NO:49); (WLRRASAP-LPDL) (SEQ ID NO:50); (WLRRASAPLPDK) (SEQ ID NO:51); (WLRRASAPLPGLS) (SEQ ID NO:52); (WLR-RASAPLPGLT) (SEQ ID NO:53); (WLRRASAPLPGKS) (SEQ ID NO:54); (WVLRRASAPLPGKT) (SEQ ID NO:55); (WLRRASAPLPDLS) (SEQ ID NO:56); (WLR-RASAPLPDLT) (SEQ ID NO:57); (WLRRSAPLPDKS) (SEQ ID NO:58); (WLRRASAPLPDKT) (SEQ ID NO:59); (RRATAPLPG) (SEQ ID NO:60); (RRATAPLPD) (SEQ ID NO:61); (RRATAPLPGL) (SEQ ID NO:62); (RRATA-PLPGK) (SEQ ID NO:63); (RRATAPLPDL) (SEQ ID NO:64); (RRATAPLPDK) (SEQ ID NO:65); (RRATA-PLPGLS) (SEQ ID NO:66); (RRATAPLPGLT) (SEQ ID NO:67); (RRATAPLPGKS) (SEQ ID NO:68); (RRATA-PLPGKT) (SEQ ID NO:69); (RRATAPLPDLS) (SEQ ID NO:70); (RRATAPLPDLT) (SEQ ID NO:71); (RRATAPLP-DKS) (SEQ ID NO:72); (RRATAPLPDKT) (SEQ ID NO:73); (LRRATAPLPG) (SEQ ID NO:74); (LRRATA-PLPD) (SEQ ID NO:75); (LRRATAPLPGL) (SEQ ID NO:76); (LRRATAPLPGK) (SEQ ID NO:77); (LRRATA- PLPDL) (SEQ ID NO:78); (LRRATAPLPDK) (SEQ id NO:79); (LRRATAPLPGLS) (SEQ ID NO:80); (LRRATAPLPGLT) (SEQ ID NO:81); (LRRATAPLPGKS) (SEQ ID NO:82); (LRRATAPLPGKT) (SEQ ID NO:83); (LRRATAPLPDLS) (SEQ ID NO:84); (LRRATAPLPDLT) (SEQ ID NO:85); (LRRATAPLPDKS) (SEQ ID NO:86); (LRRATAPLPDKT) (SEQ ID NO:87); (WLRRATAPLPG) (SEQ ID NO:88); (WLRRATAPLPD) (SEQ ID NO:89); (WLRRATAPLPGL) (SEQ ID NO:90); (WLRRATAPLPGK) (SEQ ID NO:91); (WLRRATAPLPDL) (SEQ ID NO:92); (WLRRATAPLPDK) (SEQ ID NO:93); (WLRRATAPLPGLS) (SEQ ID NO:94); (WLRRATAPLPGLT) (SEQ ID NO:95); (WLRRATAPLPGKS) (SEQ ID NO:96); (WLRRATAPLPGKT) (SEQ ID NO:97); (WLRRATAPLPDLS) (SEQ ID NO:98); (WLRRATAPLPDLT) (SEQ ID NO:99); (WLRRATAPLPDKS) (SEQ ID NO:100); (WLRRATAPLPDKT) (SEQ ID NO:101); (RRAYAPLPG) (SEQ ID NO:102); (RRAYAPLPD) (SEQ ID NO:103); (RRAYAPLPGL) (SEQ ID NO:104); (RRAYAPLPGK) (SEQ ID NO:105); (RRAYAPLPDL) (SEQ ID NO:106); (RRAYAPLPDK) (SEQ ID NO:107); (RRAYAPLPGLS) (SEQ ID NO:108); (RRAYAPLPGLT) (SEQ ID NO:109); (RRAYAPLPGKS) (SEQ ID NO:110; (RRAYAPLPGKT) (SEQ ID NO:111); (RRAYAPLPDLS) (SEQ ID NO:112); (RRAYAPLPDLT) (SEQ ID NO:113); (RRAYAPLPDKS) (SEQ ID NO:114); (RRAYAPLPDKT) (SEQ ID NO:115); (LRRAYAPLPG) (SEQ ID NO:116); (LRRAYAPLPD) (SEQ ID NO:117); (LRRAYAPLPGL) (SEQ ID NO:118); (LRRAYAPLPGK) (SEQ ID NO:119); (LRRAYAPLPDL) (SEQ ID NO:120); (LRRAYAPLPDK) (SEQ ID NO:121); (LRRAYAPLPGLS) (SEQ ID NO:122); (LRRAYAPLPGLT) (SEQ ID NO:123); (LRRAYAPLPGKS) (SEQ ID NO:124); (LRRAYAPLPGKT) (SEQ ID NO:125); (LRRAYAPLPDLS) (SEQ ID NO:126); (LRRAYAPLPDLT) (SEQ ID NO:127); (LRRAYAPLPDKS) (SEQ ID NO:128); (LRRAYAPLPDKT) (SEQ ID NO:129); (WLRRAYAPLPG) (SEQ ID NO:130); (WLRRAYAPLPD) (SEQ ID NO:131); (WLRRAYAPLPGL) (SEQ ID NO:132); (WLRRAYAPLPGK) (SEQ ID NO:133); (WLRRAYAPLPDL) (SEQ ID NO:134); (WLRRAYAPLPDK) (SEQ ID NO:135); (WLRRAYAPLPGLS) (SEQ ID NO:136); (WLRRAYAPLPGLT) (SEQ ID NO:137); (WLRRAYAPLPGKS) (SEQ ID NO:138); (WLRRAYAPLPGKT) (SEQ ID NO:139); (WLRRAYAPLPDLS) (SEQ ID NO:140); (WLRRAYAPLPDLT) (SEQ ID NO:141); (WLRRYAPLPDKS) (SEQ ID NO:142); and (WLRRAYAPLPDKT) (SEQ ID NO:143); ((F/Y/W)RRASAPLP) (SEQ ID NO:144); ((F/Y/W)RRASAPLP) (SEQ ID NO:145); ((F/Y/W)WLRRASAPLP); (SEQ ID NO:146) ((F/Y/W)RRATAPLP) (SEQ ID NO:147); ((F/Y/W)LRRATAPLP) (SEQ ID NO:148); ((F/Y/W)WLRRATAPLP) (SEQ ID NO:149); ((F/Y/W)RRAYAPLP) (SEQ ID NO:150); ((F/Y/W)LRRAYAPLP) (SEQ ID NO:151); ((F/Y/W)RRAYAPLP) (SEQ ID NO:152); ((F/Y/W)RRASAPLPG)(SEQ ID NO:153); ((F/Y/W)RRASAPLPD) (SEQ ID NO:154); ((F/Y/W)RRASAPLPGL) (SEQ ID NO:155); ((F/Y/W)RRASAPLPGK) (SEQ ID NO:156); ((F/Y/W)RRARASAPLPDL) (SEQ ID NO:157); ((F/Y/W)RRASAPLPDK)(SEQ ID NO:158); ((F/Y/W)RRASAPLPGLS) (SEQ ID NO:159); ((F/Y/W)RRASAPLPGLT) (SEQ ID NO:160); ((F/Y/W)RRASAPLPGKS); (SEQ ID NO:161); ((F/Y/W)RRASAPLPGKT) (SEQ ID NO:162); ((F/Y/W)RRASAPLPDLS) (SEQ ID NO:163); ((F/Y/W)RRSAPLPDLT) (SEQ ID NO:164); ((F/Y/W)RRASAPLPDKS) (SEQ ID NO:165); ((F/Y/W)RRASAPLPDKT) (SEQ ID NO:166); ((F/Y/W)LRRASAPLPG) (SEQ ID NO:167); ((F/Y/W)LRRASAPLPD) (SEQ ID NO:168); ((F/Y/W))LRRASAPLPGL) (SEQ ID NO:169); ((F/Y/W)LRRASAPLPGK) (SEQ ID NO:170); ((F/Y/W)LRRASAPLPDL) (SEQ ID NO:171); ((F/Y/W)LRRASAPLPDK) (SEQ ID NO:172); ((F/Y/W)LRRASAPLPGLS) (SEQ ID NO:173); ((F/Y/W)LRRASAPLPGLT) (SEQ ID NO:174); ((F/Y/W)LRRASAPLPGKS) (SEQ ID NO:175); ((F/Y/W)LRRASAPLPGKT) (SEQ ID NO:176); ((F/Y/W)LRRASAPLPDLS) (SEQ ID NO:177); ((F/Y/W)LRRASAPLPDLT) (SEQ ID NO:178); ((F/Y/W)LRRASAPLPDKS) (SEQ ID NO:179); ((F/Y/W)LRRASAPLPDKT) (SEQ ID NO:180); ((F/Y/W)WLRRASAPLPG) (SEQ ID NO:181); ((F/Y/W)WLRRASAPLPD) (SEQ ID NO:182); ((F/Y/W)WLRRASAPLPGL) (SEQ ID NO:183); ((F/Y/W)WLRRLASAPLPGK) (SEQ ID NO:184); ((F/Y/W)WLRRASAPLPDL) (SEQ ID NO:185); ((F/Y/W)WLRRASAPLPDK) (SEQ ID NO:186); ((F/Y/W)WLRRASAPLPGLS) (SEQ ID NO:187); ((F/Y/W)WLRRASAPLPGLT) (SEQ ID NO 188); ((F/Y/W)WLRRASAPLPGKS) (SEQ ID NO:189); ((F/Y/W)WLRRASAPLPGKT) (SEQ ID NO:190); ((F/Y/W)WLRRSAPLPDLS) (SEQ ID NO:191); ((F/Y/W)WLRRASAPLPDLT) (SEQ ID NO:192); ((F/Y/W)WLRRASAPLPDKS) (SEQ ID NO:193); ((F/Y/W)WLRRSAPLPDKT) (SEQ ID NO:194); ((F/Y/W)RRATAPLPG) (SEQ ID NO:195); ((F/Y/W)RRATAPLPD) (SEQ ID NO:196); ((F/Y/W)RRATAPLPGL) (SEQ ID NO:197); ((F/Y/W)RRATAPLPGK) (SEQ ID NO:198); ((F/Y/W)RRATAPLPDL) (SEQ ID NO:199); ((F/Y/W)RRATAPLPDK) (SEQ ID NO:200); ((F/Y/W)RRATAPLPGLS) (SEQ ID NO:201); ((F/Y/W)RRATAPLPGLT) (SEQ ID NO:202); ((F/Y/W)RRATAPLPGKS) (SEQ ID NO:203); ((F/Y/W)RRATAPLPGKT) (SEQ ID NO:204); ((F/Y/W)RRATAPLPDLS) (SEQ ID NO:205); ((F/Y/W)RRATAPLPDLT) (SEQ ID NO:206); ((F/Y/W)RRATAPLPDKS) (SEQ ID NO:207); ((F/Y/W)RRATAPLPDKT) (SEQ ID NO:208); ((F/Y/W)LRRATAPLPG) (SEQ ID NO:209); ((F/Y/W)LRRATAPLPD) (SEQ ID NO:210); ((F/Y/W)LRRATAPLPGL) (SEQ ID NO:211); ((F/Y/W)LRRATAPLPGK) (SEQ ID NO:212); ((F/Y/W)LRRATAPLPDL) (SEQ ID NO:213); ((F/Y/W)LRRATAPLPDK) (SEQ ID NO:214); ((F/Y/W)LRRATAPLPGLS) (SEQ ID NO:215); ((F/Y/W)LRRATAPLPGLT) (SEQ ID NO:216); ((F/Y/W)LRRTAPLPGKS) (SEQ ID NO:217); ((F/Y/W)LRRATAPLPGKT) (SEQ ID NO:218); ((F/Y/W)LRRATAPLPDLS) (SEQ ID NO:219); ((F/Y/W)LRRATAPLPDLT) (SEQ ID NO:220); ((F/Y/W)LRRATAPLPDKS) (SEQ ID NO:221); ((F/Y/W)LRRATAPLPDKT) (SEQ ID NO:222); ((F/Y/W)WLRRATAPLPG) (SEQ ID NO:223); ((F/Y/W)WLRRATAPLPD) (SEQ ID NO:224); ((F/Y/W)WLRRATAPLPGL) (SEQ ID NO:225); ((F/Y/W)WLRRATAPLPGK) (SEQ ID NO:226); ((F/Y/W)WLRRATAPLPDL) (SEQ ID NO:227); ((F/Y/W)WLRRATAPLPDK) (SEQ ID NO:228); ((F/Y/W)WLRRATAPLPGLS) (SEQ ID NO:229); ((F/Y/W)WLRRATAPLPGLT) (SEQ ID NO:230); ((F/Y/W)WLRRATAPLPGKS) (SEQ ID NO:231); ((F/Y/W)WLRRATAPLPGKT) (SEQ ID NO:232); ((F/Y/W)WLRRATAPLPDLS)(SEQ ID NO:233); ((F/Y/W)WLRRATAPLPDLT) (SEQ ID NO:234); ((F/Y/W)WLRRATAPLPDKS) (SEQ ID NO:235); ((F/Y/W)WLRRATAPLPDKT) (SEQ ID NO:236); ((F/Y/W)RRAYAPLPG) (SEQ ID NO:237); ((F/Y/W)RRAYAPLPD) (SEQ ID NO:238); ((F/Y/W)RRAYAPLPGL) (SEQ ID NO:239); ((F/Y/W)RRAYAPLPGK) (SEQ ID NO:240); ((F/Y/W)RRAYAPLPDL) (SEQ ID NO:241); ((F/Y/W)RRAYAPLPDK) (SEQ ID NO:242); ((F/Y/W)RRAYAPLPGLS) (SEQ ID NO:243); ((F/Y/W)RRAYAPLPGLT) (SEQ ID NO:244); ((F/Y/W)RRAYAPLPGKS) (SEQ ID NO:245); ((F/Y/W)RRYAPLPGKT) (SEQ ID NO:246); (F/Y/W) RRAYAPLPDLS) (SEQ ID NO:247); ((F/Y/W)RRAYAPLPDLT) (SEQ ID NO:248); ((F/Y/W)RRAYAPLPDKS) (SEQ ID NO:249); ((F/Y/W)RRAYAPLPDKT) (SEQ ID NO:250)); ((F/Y/W)LRRAYAPLPG) (SEQ ID NO:251); ((F/Y/W)LRRAYAPLPD) (SEQ ID NO:252); ((F/Y/W)LRRAYAPLPGL) (SEQ ID NO:253); ((F/Y/W)LRRAYAPLPGK) (SEQ ID NO:254); ((F/Y/W)LRRAYAPLPDL) (SEQ ID NO:255); ((F/Y/W)LRRAYAPLPDK) (SEQ ID NO:256); ((F/Y/W)LRRAYAPLPGLS) (SEQ ID NO:257); ((F/Y/W)LRRAYAPLPGLT) (SEQ ID NO:258); ((F/Y/W)LRRAYAPLPGKS) (SEQ ID NO:259); ((F/Y/W)LRRAYAPLPGKT) (SEQ ID NO:260); ((F/Y/W)LRRAYAPLPDLS) (SEQ ID NO:261); ((F/Y/W)LRRAYAPLPDLT) (SEQ ID NO:262); ((F/Y/W)LRRAYAPLPDKS) (SEQ ID NO:263); ((F/Y/W)LRRAYAPLPDKT) (SEQ ID NO:264); ((F/Y/W)WLRRAYAPLPG) (SEQ ID NO:265); ((F/Y/W)WLRRAYAPLPD) (SEQ ID NO:266); ((F/Y/W)WLRRAYAPLPGL) (SEQ ID NO:267); ((F/Y/W)WLRRAYAPLPGK) (SEQ ID NO:268); ((F/Y/W)WLRRAYAPLPDL) (SEQ ID NO:269); ((F/Y/W)WLRRAYAFPLPDK) (SEQ ID NO:270); ((F/Y/W)WLRRAYAPLPGLS) (SEQ ID NO:271); ((F/Y/W)WVLRRAYAPLPGLT) (SEQ ID NO:272); ((F/Y/W)WLRRAYAPLPGKS) (SEQ ID NO:273); ((F/Y/W)WLRRAYAPLPGKT) (SEQ ID NO:274); ((F/Y/W)WLRRAYAPLPDLS) (SEQ ID NO:275); ((F/Y/W)WLRRAYAPLPDLT) (SEQ ID NO:276); ((F/Y/W)WLRRAYAPLPDKS) (SEQ ID NO:277); and ((F/Y/W)WLRRAYAPLPDKT) (SEQ ID NO:278) wherein (F/Y/W) means that the residue is selected from F, Y, and W. Other specific polypeptides falling within the scope of general formula I will be readily apparent to one of skill in the art based on the teachings herein.

The polypeptides of general formula I may be present in multiple copies to provide increased efficacy for use in the methods of the invention. For example, the polypeptides may be present in 1, 2, 3, 4, or 5 copies. In a further embodiment, the polypeptides comprising a sequence according to general formula I comprise a combination of different sequences from the region X1-A(X2)APLP—X3. In this embodiment, for example, the polypeptide can consist of 1 copy of SEQ ID NO: 9 and 1 copy of SEQ ID NO: 143. In a different example, the polypeptide could consist of 2 copies of SEQ ID NO: 200 and 3 copies of SEQ ID NO: 62. It will be apparent to one of skill in the art that many such combinations are possible based on the teachings of the present invention.

In a preferred embodiment, the polypeptides according to general formula I further comprise one or more transduction domains. As used herein, the term "transduction domain" means an amino acid sequence that can carry the polypeptide across cell membranes. These domains can be linked to other polypeptides to direct movement of the linked polypeptide across cell membranes. In some cases the transducing molecules do not need to be covalently linked to the active polypeptide. In a preferred embodiment, the transduction domain is linked to the rest of the polypeptide via peptide bonding. Examples of such transduction domains include, but are not limited to $(R)_{4-9}$ (SEQ ID NO:279); GRKKRQRRRPPQ (SEQ ID NO:280); YARAAARQARA (SEQ ID NO:281); DAATATRGRSAASRPTERPRAPARSASRPRRPVE (SEQ ID NO:282); GWTLNSAGYLLGLINLKALAALAKKIL (SEQ ID NO:283); PLSSIFSRIGDP (SEQ ID NO:284); AAVALLPAVLLALLAP (SEQ ID NO:285); AAVLLPVLLAAP (SEQ ID NO:286); VTVLALGALAGVGVG (SEQ ID NO:287); GALFLGWLGAAGSTMGAWSQP (SEQ ID NO:288); GWTLNSAGYLLGLINLKALAALAKKIL (SEQ ID NO:289); KLALKLALKAALKLA (SEQ ID NO:290); KETWWETWWTEWSQPKKKRKV (SEQ ID NO:291); KAFAKLAARLYRKAGC (SEQ ID NO:292); KAFAKLAARLYRAAGC (SEQ ID NO:293); AAFAKLAARLYRKAGC (SEQ ID NO:294); KAFAALAARLYKAGC (SEQ ID NO:295); KAFAKLAAQLYRKAGC (SEQ ID NO:296), GGGGYGRKKRRQRRR (SEQ ID NO:297), and YGRKKRRQRRR (SEQ ID NO:299).

In a further embodiment, the polypeptides comprise or consist of polypeptides of the formula:

B1-X1-A(X2)APLP—X3-B2 wherein X1, X2, and X3 are as defined above, and wherein B1 and B2 are independently absent or comprise a transduction domain, as described above.

In a preferred embodiment, one or both of B1 and B2 comprise or consist of the amino acid sequence of YGRKKRRQRRR (SEQ ID NO:299) and/or YARAAARQARA (SEQ ID NO:281). In a most preferred embodiment, the polypeptide according to the general formulas disclosed herein comprises or consists of a polypeptide according to YGRKKRQRRRWLRRApSAPLPGL (SEQ ID NO:301) or YARAARQARAWLRRApSAPLPGL (SEQ ID NO:315), wherein "pS" represents a phosphorylated serine residue.

In a further embodiment of the methods of the present invention, the polypeptides comprise or consist of polypeptides of the formula:

J1-J2-X1-A(X2)APLP—X3-J3 wherein X1, X2, and X3 are as defined above, wherein J2 and J3 are independently absent or comprise a transduction domain, as described above, and wherein J1 is absent or is one or more molecules comprising one or more aromatic ring, as discussed above.

The polypeptides for use in the methods of the invention can further be derivatized to provide enhanced half-life, for example, by linking to polyethylene glycol. The polypeptides of the invention may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare polypeptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such polypeptides are resistant to protease activity, and possess an extended half-live in vivo.

The term "polypeptide" is used in its broadest sense to refer to a sequence of subunit amino acids, amino acid analogs, or peptidomimetics. The subunits are linked by peptide bonds, although the polypeptide can comprise further moieties that are not necessarily linked to the polypeptide by a peptide bond. For example, as discussed above, the polypeptide can further comprise a non-amino acid molecule that contains an aromatic ring.

The polypeptides described herein may be chemically synthesized or recombinantly expressed. Recombinant expression can be accomplished using standard methods in the art, generally involving the cloning of nucleic acid sequences capable of directing the expression of the polypeptides into an expression vector, which can be used to transfect or transduce a host cell in order to provide the cellular machinery to carry out expression of the polypeptides. Such expression vectors can comprise bacterial or viral expression vectors, and such host cells can be prokaryotic or eukaryotic.

Preferably, the polypeptides for use in the methods of the present invention are chemically synthesized. Synthetic polypeptides, prepared using the well-known techniques of solid phase, liquid phase, or peptide condensation techniques, or any combination thereof, can include natural and unnatural amino and unnatural amino acids. Amino acids used for peptide synthesis may be standard Boc (Nα-amino protected Nα-t-butyloxycarbonyl) amino acid resin with the standard deprotecting, neutralization, coupling and wash protocols of standard solid phase procedure, or base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art.

Solid phase peptide synthesis may be accomplished by techniques familiar to those in the art and provided, for example by using automated synthesizers.

As used herein, an "individual in need thereof" is an individual that has suffered or will suffer (for example, via a surgical procedure) a wound that may result in scar formation, or has resulted in scar formation. As used herein, the term "wound" refers broadly to injuries to the skin and subcutaneous tissue, but does not include wounds to blood vessels or heart tissue.

Such wounds include, but are not limited to lacerations; burns; punctures; pressure sores; bed sores; canker sores; trauma, bites; fistulas; ulcers; lesions caused by infections; periodontal wounds; endodontic wounds; burning mouth syndrome; laparotomy wounds; surgical wounds; incisional wounds; contractures after burns; tissue fibrosis, including but not limited to idiopathic pulmonary fibrosis, hepatic fibrosis, renal fibrosis, retroperitoneal fibrosis, and cystic fibrosis, but excluding blood vessel fibrosis or heart tissue fibrosis; and wounds resulting from cosmetic surgical procedures. As used herein, the phrase "reducing scar formation" means any decrease in scar formation that provides a therapeutic or cosmetic benefit to the patient. Such a therapeutic or cosmetic benefit can be achieved, for example, by decreasing the size and/or depth of a scar relative to scar formation in the absence of treatment with the methods of the invention, or by reducing the size of an existing scar.

As used herein, such scars include scars of all types, including but not limited to keloids; hypertrophic scars; and adhesion formation between organ surfaces, including but not limited to those occurring as a result of surgery.

The present invention, by providing methods for reducing scar formation, will be clinically useful for treating all types of wounds to reduce scar formation, both for reducing initial scar formation, and for therapeutic treatment of existing scars (i.e.: cutting out the scar after its formation, treating it with the compounds of the invention, and letting the scar heal more slowly). Such wounds are as described above. As used herein, the phrase "promoting wound healing" means any increase in wound healing that provides a therapeutic or cosmetic benefit to the patient. Such a therapeutic benefit can be achieved, for example, by one or more of increasing the rate of wound healing and/or increasing the degree of wound healing relative to an untreated individual. Such wounds are as described above.

In a preferred embodiment, the individual is a mammal; in a more preferred embodiment, the individual is a human.

While not being limited to a specific mechanism of action, the inventors believe that the beneficial effect off the methods of the invention in promoting wound healing and/or reducing scar formation are due to reduction of wound contraction within the wound area, which limits scar formation that accompanies wound healing, and increase in blood flow to the wound area.

As used herein, an "amount effective" of the one or more polypeptides is an amount that is sufficient to provide the intended benefit of treatment. An effective amount of the polypeptides that can be employed ranges generally between about 0.01 μg/kg body weight and about 10 mg/kg body weight, preferably ranging between about 0.05 μg/kg and about 5 mg/kg body weight. However dosage levels are based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods.

The polypeptides may be subjected to conventional pharmaceutical operations such as sterilization and/or may contain conventional adjuvants, such as preservatives, stabilizers, wetting agents, emulsifiers, buffers etc.

For administration, the polypeptides are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The polypeptides or pharmaceutical compositions thereof may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Preferred embodiments for administration vary with respect to the condition being treated. In a preferred embodiment, the polypeptides or pharmaceutical compositions are disposed on or in a wound dressing or other topical administration. Such wound dressings can be any used in the art, including but not limited to films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), cellophane, and biological polymers such as those described in US patent application publication number 20030190364, published Oct. 9, 2003.

The polypeptides may be made up in a solid form (including granules, powders or suppositories) or in a liquid form (e.g., solutions, suspensions, or emulsions). The polypeptides of the invention may be applied in a variety of solutions. Suitable solutions for use in accordance with the invention are sterile, dissolve sufficient amounts of the polypeptides, and are not harmful for the proposed application.

Example 1

Actin Cytoskeleton Disruption

Materials and Methods
Peptide Synthesis and Purification

Peptides were synthesized using standard f-moc chemistry and purified using high performance liquid chromatography (HPLC) by Cell Essentials (Boston, Mass.). Fluorescent peptides were synthesized with a fluorescein isothiocyanate (FITC) labeled on the N terminus, using β-alanine as a linker.
Cell Culture, Immunocytochemistry, and Interference Reflection Microscopy Unless otherwise stated, all reagents were purchased from Sigma, St. Louis, Mo., Swiss Albino 3T3 fibroblasts (ATCC, Manassas, Va.) were cultured in DMEM supplemented with 10% BCS, 4 mM L-glutamine and 50 µg/ml penicillin-streptomycin and maintained at 37° C., 5% $CO_2$. Cells were seeded and cultured overnight. Culture media was replaced with DMEM containing 0.5% BCS 1 hour prior to experimentation. Cells were incubated with the peptide analogues or reagent (LPA or forskolin) diluted in DMEM containing 0.5% BCS, 30 minutes at 37° C. Cells were then fixed in 4% paraformaldehyde, permeabilized in 0.25% Triton X-100, and blocked with 1% BSA solution for 1 hour. To determine f-actin cytoskeletal distribution, treated cells were incubated with Alexa 568 phalloidin (Molecular Probes, Eugene, Oreg.) in 1% BSA, 30 minutes. To determine focal adhesion protein localization, treated cells were incubated with primary monoclonal antibodies for α-actinin (1:100, Upstate, Charlottesville, Va.), vinculin (1:100, Sigma) or paxillin (1:100, BD Bioscience-Transduction Labs, San Jose, Calif.) in 1% BSA solution for 2 hours, rinsed in PBS and incubated 60 rain with Cy3-goat IgG secondary antibody (Jackson ImmunoResearch, West Grove, Pa.). Slides were mounted and analyzed by confocal microscopy (Leica TCS SP2, Bannockburn, Ill.). Interference reflection microscopy was used to determine the percentage of 3T3 cells positive for focal adhesions. Cells were cultured as described above and either untreated or treated with 100 nM Hep I (thrombospondin peptide), 10 µM and 25 µM pHSP20 (phospho HSP20 peptide) or 10 µM and 25 µM sHSP20 (scrambled HSP20 peptide).
Results Cellular processes such as cell adhesion, cytokinesis, cell motility, migration, and muscular contraction/relaxation require dynamic reorganization of the actin cytoskeleton. Activation of cyclic nucleotide signaling pathways in various cell types leads to profound alterations in the cytoskeleton, which include loss of central stress fibers, and focal adhesion plaques; cytoplasmic retraction with the formation of thin processes; and rounding of the cell bodies (1). In aggregate, these changes lead to a star-shaped appearance that has been termed "stellation."

The cyclic nucleotide signaling pathways include adenylate cyclase/cAMP/cAMP-dependent protein kinase (PKA) and guanylate cyclase/cGMP/cGMP-dependent protein kinase (PKG). These pathways converge at the phosphorylation of the small heat shock-related protein, HSP2 on serine 16 (2, 3). To determine if HSP20 mediates cyclic nucleotide-dependent stellation, phosphopeptide analogues of HSP20 (pHSP20) were synthesized (4) that contained: 1) the amino acid sequence surrounding the phosphorylation site of HSP20 (WLRRApSAPLPGL) (SEQ ID NO:300); 2) a phosphoserine (pS); and 3) an 11 amino acid protein transduction domain from the HIV Tat protein (YGRKKRRQRRR) (SEQ ID NO:299). The sequence of the resulting test polypeptide is YGRKKRRQRRRWLRRApSAPLPGL (SEQ ID NO:301). Control peptides contained the same sequence as the phosphopeptide analogues except with either an alanine in place of the phosphoserine (aHSP20) or a scrambled HSP20 sequence containing phosphoserine (scrHSP20, PRpSLWALGRPL-SAK) (SEQ ID NO:302).

Swiss albino 3T3 cells were either untreated or treated with 10 µM LPA, 10 µM forskolin, 25 µM FITC-pHSP20, or 25 µM FITC-aHSP20 as described (4). Cells were fixed, stained for f-actin using Alexa 568 phalloidin, and visualized by projection images of confocal fluorescence microscopy. FITC-peptide fluorescence was overlayed with actin staining to show colocalization. Cells that had been exposed to serum (10%) or lysophosphatidic acid (10 µM, 30 min) displayed robust stress fibers. Cells that were treated with the adenylate cyclase activator forskolin (10 µM, 30 min) or with pHSP20 displayed stellate morphology and disrupted stress fibers. The control peptide aHSP20 did not lead to alterations in morphology or stress fibers.

To confirm that the loss of stress fibers is associated with loss of filamentous (f-) actin and commensurate increases in globular (g-) actin, a DNase 1 inhibition assay was performed (5). 3T3 cells were cultured and treated as indicated (4). Monomer g-actin was biochemically quantitated using a DNase 1 inhibition assay. The level of g-actin in the cell extract that caused 50% inhibition of DNase 1 was estimated from a standard actin curve that was determined using known amounts of actin. Forskolin (10 µM, 30 min) and pHSP20 (25 µM, 30 min) treatment led to increases in g-actin (FIG. 1). Thus, transduction of pHSP20 led to similar changes in actin filament dynamics and cellular morphology, as did activation of the upstream adenylate cyclase activator forskolin.

To further verify disruption of the actin cytoskeletal network upon addition of pHSP20, the presence of focal adhesions was examined by interference reflection microscopy (6, 7). Focal adhesions are plaque-like scaffolds of both structural and signaling proteins that link the cytoskeleton to the extracellular matrix through integrin and syndecan receptors. Focal adhesions are formed in response to cell adhesion and involve signaling through Rho. These are dynamic structures that undergo disassembly and restructuring, characterized by loss of stress fibers and dispersion of vinculin, α-actinin, and paxillin, and are associated with increased cell motility. The matricellular proteins thrombospondin and tenascin-C cause focal adhesion disassembly and introduction of the intermediate cell adhesive state in a manner that requires basal PKG activity (7).

Swiss albino 3T3 cells were either untreated, or treated for 30 rain with 10 µM LPA, 10 µM forskolin, 25 µM pHSP20, 25 µM FITC-aHSP20, and immunostained for α-actinin, vinculin, or paxillin. Confocal projection images for FITC-peptides were overlayed with actin staining to show colocalization (f, i). Scale bar 50 µm.

Cells treated with forskolin or pHSP20 displayed a decrease in focal adhesion accumulations of α-actinin, vinculin, and paxillin, while cells treated with aHSP20 appeared to retain focal adhesion proteins. The pHSP20 led to disruption of focal adhesions in cultured 3T3 cells similar to the loss of focal adhesions that occurred with the hep I peptide of thrombospondin (FIG. 2), which has been shown to signal focal adhesion disassembly in a PKG-dependent manner (7).

Again, aHSP20 had no effect on focal adhesions. These data suggest that phosphorylated HSP20 might be one of the downstream effectors by which PKG mediates focal adhesion disruption. These experiments further suggest that HSP20 and functionally equivalent polypeptides thereof, are useful for promoting wound healing and/or reducing scar formation.

REFERENCES FOR EXAMPLE 1

1. G. J. Ramakers, W. H. Moolenaar, *Exp. Cell Res.* 245, 252 (1998).
2. A. Beall et al., *J. Biol. Chem.* 274, 11344 (1999).
3. C. R. Flynn et al., *Faseb J.* 17, 1358 (2003).
4. Materials and methods are available as supporting material on *Science* Online.
5. C. S. Heacock, J. R. Bamburg, *Anal. Biochem.* 135, 22 (1983).
6. J. E. Murphy-Ullrich, S. Gurusiddappa, W. A. Frazier, M. Hook, *J. Biol. Chem.* 268, 26784 (1993).
7. J. E. Murphy-Ullrich et al, *J. Cell. Sci.* 109, 2499 (1996).

Example 2

Enhancing Neural Electrode Durability

The durability of neural recording electrodes depends on scar formation. The scar formation in neural tissue is referred to as gliosis or glial scarring and results in insulation of the electrode from the neuronal tissues. These electrodes are often implanted into the brain for long-term monitoring of neuronal population activities for investigation of motor control or stimulation for treatment of neural trauma or diseases. In order to achieve the full potential of neural recording electrodes, methods must be developed to reduce scar formation and improve the interface between the electrode and the electrically active neurons. The reduction of scar formation will improve both short- and long-term recording potential of the electrodes. Modulation of scar tissue formation around neural electrodes will improve function of stimulating electrodes as will including deep brain electrodes for Parkinson's disease, cochlear implants, and spinal cord stimulators. Since scar tissue acts as an insulator, improved conduction of action potentials to the electrodes will improve the performance of all implanted neural electrodes.

Neural Recording Electrodes:

Electrodes, when implanted into the brain, become encapsulated over time. Two biological responses result in encapsulation. The first involves the formation of a compact barrier of fibroblasts and extracellular matrix around the electrode. The second, gliosis, involves the glial cells of the brain. Gliosis is characterized by phenotypic modulation of astrocytes into glial cells, which produce extracellular matrix and further promote scar formation. There is a correlation between tissue trauma and degree of capsule formation with thicker capsules being formed in areas of higher tissue trauma. The increased trauma leads to disruption of the blood-brain barrier, which in turn, introduces blood-borne molecules into the brain. Glial scars, or capsules, can be up to 250 μm thick. These capsules act as insulators, impeding the conduction of electrical signals from neurons to the recording electrodes, thus limiting the function of the electrodes.

Inhibiting astrocyte proliferation and extracellular matrix formation around the site of electrodes will increase both the longevity and strength of the recording signals. Upon exposure to blood-borne factors, astrocytes exhibit morphological changes, which include stress fiber formation and loss of stellation. Stellation is a term used to describe alterations to the actin cytoskeleton that result in cells adopting a star-like or stellate shape. Upon loss of stellate morphology, astrocytes proliferate and secrete extracellular matrix proteins, which forms glial scars. Lysophosphatidic acid, a lipid found in high concentrations in blood, has been associated with the loss of stellate morphology, astrocytes proliferation, and gliosis.

Lysophosphatidic acid (LPA) is a biologically active signaling molecule that is bound to serum albumin in the blood. LPA can reverse stellation in astrocytes; this is likely due to inhibition of the cAMP pathway. LPA also can cause neurite retraction. HSP20 is the substrate molecule of both the cAMP and cGMP pathways and that its phosphorylation at serine 16 results in disruption of actin filaments.

Microwire arrays were implanted in the motor cortex of Sprague Dawley rats. Six male Sprague-Dawley rats (300-450 g) were implanted with 2×4 arrays of 50 μm tungsten wire. The electrodes were spaced 500 um apart for a total array size of approximately 1.5 mm×0.5 mm. The implant was centered +3 mm anterior and +2 mm lateral from bregma. The craniotomy was opened slightly larger than the implant size and an injection (0.1 cc, 0.9% PBS or 100 μm p20) was made into the arachnoid space near the implant site using a 30 gauge needle. The microwire array was held in a micromanipulator and lowered 2 mm from the surface of the dura. The craniotomy was covered with Gelfoam® and the implant and connector were cemented in place with dental acrylic. Three groups were implanted and evaluated histologically after four weeks. Group one was implanted with untreated electrodes. Group two was implanted with dextran coated microwire electrodes and group three was implanted with dextran coated electrodes and received a subdural injection of the HSP20 biomimetic peptide (YGRKKRRQRRRWLRRApSAP-LPGL (SEQ ID NO:301). At 4 weeks two animals from each group were sacrificed for histology. Animals were anesthetized and perfused with PBS followed by formalin. The brain tissue was dissected from the skull and sectioned into 100 μM sections using a vibrotome. Sections were permeabilized with 0.05% triton and blocked with bovine serum albumin followed by probing with rabbit anti-glial fibrillary acidic protein (GFAP) for astrocytes and goat anti-microtubule associated protein 2 (MAP2) for axons. Texas Red labeled anti-Rabbit and Cy5 labeled anti-donkey secondary antibodies were used respectively for visualization.

While significant glial scarring was seen with neural electrodes alone at four weeks, reduced scarring was seen with dextran coated electrodes. For the electrodes implanted with the addition of the HSP20 biomimetic peptide, essentially no scarring was observed; in addition, a higher density of axons was seen in the vicinity of the microwire electrodes. This data suggests that the HSP20 peptide is effective at both inhibiting scarring around the electrodes and enhancing axon survival in the vicinity of the implant, and further suggest that HSP20 and functionally equivalent polypeptides thereof are useful for promoting wound healing and/or reducing scar formation.

SEQUENCE LISTING

<160> NUMBER OF SEQ ID NOS: 321

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Leu Arg Arg
1

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Thr, Tyr, Asp, Glu, Hydroxy-Lys,
      Hydroxy-Pro, Phospho-Ser or Phospho-Tyr

<400> SEQUENCE: 2

Ala Xaa Ala Pro Leu Pro
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ser Ala Pro Leu Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Thr Ala Pro Leu Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Ala Pro Leu Pro
1               5

<210> SEQ ID NO 6

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Thr Ala Pro Leu Pro
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Tyr Ala Pro Leu Pro
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Tyr Ala Pro Leu Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Ala Ser Ala Pro Leu Pro
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Arg Arg Ala Ser Ala Pro Leu Pro
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
Trp Leu Arg Arg Ala Ser Ala Pro Leu Pro
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Arg Ala Thr Ala Pro Leu Pro
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg Arg Ala Thr Ala Pro Leu Pro
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Leu Arg Arg Ala Thr Ala Pro Leu Pro
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Ala Tyr Ala Pro Leu Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Arg Arg Ala Tyr Ala Pro Leu Pro
1               5

<210> SEQ ID NO 17
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 17

Trp Leu Arg Arg Ala Tyr Ala Pro Leu Pro
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Ala Ser Ala Pro Leu Pro Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Ala Ser Ala Pro Leu Pro Asp
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Ala Ser Ala Pro Leu Pro Gly Leu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Arg Ala Ser Ala Pro Leu Pro Gly Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Ala Ser Ala Pro Leu Pro Asp Leu
1               5                   10

```
<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Arg Ala Ser Ala Pro Leu Pro Asp Lys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Ala Ser Ala Pro Leu Pro Gly Leu Ser
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Ala Ser Ala Pro Leu Pro Gly Leu Thr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Ala Ser Ala Pro Leu Pro Gly Lys Ser
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Ala Ser Ala Pro Leu Pro Gly Lys Thr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
Arg Arg Ala Ser Ala Pro Leu Pro Asp Leu Ser
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Ala Ser Ala Pro Leu Pro Asp Leu Thr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Ala Ser Ala Pro Leu Pro Asp Lys Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Ala Ser Ala Pro Leu Pro Asp Lys Thr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Arg Arg Ala Ser Ala Pro Leu Pro Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg Arg Ala Ser Ala Pro Leu Pro Asp
1               5                   10

<210> SEQ ID NO 34
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 34

Leu Arg Arg Ala Ser Ala Pro Leu Pro Gly Leu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Arg Ala Ser Ala Pro Leu Pro Gly Lys
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Arg Arg Ala Ser Ala Pro Leu Pro Asp Leu
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Arg Arg Ala Ser Ala Pro Leu Pro Asp Lys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Arg Arg Ala Ser Ala Pro Leu Pro Gly Leu Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Arg Arg Ala Ser Ala Pro Leu Pro Gly Leu Thr
1               5                   10
```

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Arg Arg Ala Ser Ala Pro Leu Pro Gly Lys Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Arg Arg Ala Ser Ala Pro Leu Pro Gly Lys Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Arg Arg Ala Ser Ala Pro Leu Pro Asp Leu Ser
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Arg Arg Ala Ser Ala Pro Leu Pro Asp Leu Thr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Arg Arg Ala Ser Ala Pro Leu Pro Asp Lys Ser
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Leu Arg Arg Ala Ser Ala Pro Leu Pro Asp Lys Thr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Leu Arg Arg Ala Ser Ala Pro Leu Pro Gly
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Leu Arg Arg Ala Ser Ala Pro Leu Pro Asp
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Leu Arg Arg Ala Ser Ala Pro Leu Pro Gly Leu
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Leu Arg Arg Ala Ser Ala Pro Leu Pro Gly Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Leu Arg Arg Ala Ser Ala Pro Leu Pro Asp Leu
1               5                   10

<210> SEQ ID NO 51
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 51

Trp Leu Arg Arg Ala Ser Ala Pro Leu Pro Asp Lys
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Leu Arg Arg Ala Ser Ala Pro Leu Pro Gly Leu Ser
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Leu Arg Arg Ala Ser Ala Pro Leu Pro Gly Leu Thr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Leu Arg Arg Ala Ser Ala Pro Leu Pro Gly Lys Ser
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Leu Arg Arg Ala Ser Ala Pro Leu Pro Gly Lys Thr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Leu Arg Arg Ala Ser Ala Pro Leu Pro Asp Leu Ser
1               5                   10
```

```
<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Leu Arg Arg Ala Ser Ala Pro Leu Pro Asp Leu Thr
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Leu Arg Arg Ala Ser Ala Pro Leu Pro Asp Lys Ser
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Leu Arg Arg Ala Ser Ala Pro Leu Pro Asp Lys Thr
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Arg Ala Thr Ala Pro Leu Pro Gly
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Arg Ala Thr Ala Pro Leu Pro Asp
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 62

Arg Arg Ala Thr Ala Pro Leu Pro Gly Leu
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Arg Ala Thr Ala Pro Leu Pro Gly Lys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Arg Ala Thr Ala Pro Leu Pro Asp Leu
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Arg Ala Thr Ala Pro Leu Pro Asp Lys
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Arg Ala Thr Ala Pro Leu Pro Gly Leu Ser
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Arg Ala Thr Ala Pro Leu Pro Gly Leu Thr
1               5                   10

<210> SEQ ID NO 68
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Arg Ala Thr Ala Pro Leu Pro Gly Lys Ser
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Arg Ala Thr Ala Pro Leu Pro Gly Lys Thr
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Arg Ala Thr Ala Pro Leu Pro Asp Leu Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Arg Ala Thr Ala Pro Leu Pro Asp Leu Thr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Arg Ala Thr Ala Pro Leu Pro Asp Lys Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Arg Ala Thr Ala Pro Leu Pro Asp Lys Thr
```

```
<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Arg Arg Ala Thr Ala Pro Leu Pro Gly
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Arg Arg Ala Thr Ala Pro Leu Pro Asp
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Arg Arg Ala Thr Ala Pro Leu Pro Gly Leu
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Arg Arg Ala Thr Ala Pro Leu Pro Gly Lys
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Arg Arg Ala Thr Ala Pro Leu Pro Asp Leu
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 79

Leu Arg Arg Ala Thr Ala Pro Leu Pro Asp Lys
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Arg Arg Ala Thr Ala Pro Leu Pro Gly Leu Ser
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Arg Arg Ala Thr Ala Pro Leu Pro Gly Leu Thr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Arg Arg Ala Thr Ala Pro Leu Pro Gly Lys Ser
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Arg Arg Ala Thr Ala Pro Leu Pro Gly Lys Thr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Arg Arg Ala Thr Ala Pro Leu Pro Asp Leu Ser
1               5                   10

<210> SEQ ID NO 85
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Arg Arg Ala Thr Ala Pro Leu Pro Asp Leu Thr
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Arg Arg Ala Thr Ala Pro Leu Pro Asp Lys Ser
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Arg Arg Ala Thr Ala Pro Leu Pro Asp Lys Thr
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Trp Leu Arg Arg Ala Thr Ala Pro Leu Pro Gly
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Leu Arg Arg Ala Thr Ala Pro Leu Pro Asp
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90
```

Trp Leu Arg Arg Ala Thr Ala Pro Leu Pro Gly Leu
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Leu Arg Arg Ala Thr Ala Pro Leu Pro Gly Lys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Leu Arg Arg Ala Thr Ala Pro Leu Pro Asp Leu
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Leu Arg Arg Ala Thr Ala Pro Leu Pro Asp Lys
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Leu Arg Arg Ala Thr Ala Pro Leu Pro Gly Leu Ser
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Leu Arg Arg Ala Thr Ala Pro Leu Pro Gly Leu Thr
1               5                   10

<210> SEQ ID NO 96
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 96

Trp Leu Arg Arg Ala Thr Ala Pro Leu Pro Gly Lys Ser
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Trp Leu Arg Arg Ala Thr Ala Pro Leu Pro Gly Lys Thr
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Leu Arg Arg Ala Thr Ala Pro Leu Pro Asp Leu Ser
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Trp Leu Arg Arg Ala Thr Ala Pro Leu Pro Asp Leu Thr
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Leu Arg Arg Ala Thr Ala Pro Leu Pro Asp Lys Ser
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Trp Leu Arg Arg Ala Thr Ala Pro Leu Pro Asp Lys Thr
1               5                   10

```
<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Arg Ala Tyr Ala Pro Leu Pro Gly
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Arg Ala Tyr Ala Pro Leu Pro Asp
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Arg Ala Tyr Ala Pro Leu Pro Gly Leu
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Arg Ala Tyr Ala Pro Leu Pro Gly Lys
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Arg Ala Tyr Ala Pro Leu Pro Asp Leu
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107
```

Arg Arg Ala Tyr Ala Pro Leu Pro Asp Lys
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Arg Ala Tyr Ala Pro Leu Pro Gly Leu Ser
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Arg Ala Tyr Ala Pro Leu Pro Gly Leu Thr
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Arg Ala Tyr Ala Pro Leu Pro Gly Lys Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Arg Ala Tyr Ala Pro Leu Pro Gly Lys Thr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Arg Ala Tyr Ala Pro Leu Pro Asp Leu Ser
1               5                   10

<210> SEQ ID NO 113
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 113

Arg Arg Ala Tyr Ala Pro Leu Pro Asp Leu Thr
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Arg Ala Tyr Ala Pro Leu Pro Asp Lys Ser
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Arg Ala Tyr Ala Pro Leu Pro Asp Lys Thr
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Leu Arg Arg Ala Tyr Ala Pro Leu Pro Gly
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Leu Arg Arg Ala Tyr Ala Pro Leu Pro Asp
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Arg Arg Ala Tyr Ala Pro Leu Pro Gly Leu
1               5                   10
```

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Leu Arg Arg Ala Tyr Ala Pro Leu Pro Gly Lys
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Leu Arg Arg Ala Tyr Ala Pro Leu Pro Asp Leu
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Arg Arg Ala Tyr Ala Pro Leu Pro Asp Lys
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Arg Arg Ala Tyr Ala Pro Leu Pro Gly Leu Ser
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Leu Arg Arg Ala Tyr Ala Pro Leu Pro Gly Leu Thr
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 124

Leu Arg Arg Ala Tyr Ala Pro Leu Pro Gly Lys Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Leu Arg Arg Ala Tyr Ala Pro Leu Pro Gly Lys Thr
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Arg Arg Ala Tyr Ala Pro Leu Pro Asp Leu Ser
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Leu Arg Arg Ala Tyr Ala Pro Leu Pro Asp Leu Thr
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Arg Arg Ala Tyr Ala Pro Leu Pro Asp Lys Ser
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Arg Arg Ala Tyr Ala Pro Leu Pro Asp Lys Thr
1               5                   10

<210> SEQ ID NO 130
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 130

Trp Leu Arg Arg Ala Tyr Ala Pro Leu Pro Gly
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Trp Leu Arg Arg Ala Tyr Ala Pro Leu Pro Asp
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Trp Leu Arg Arg Ala Tyr Ala Pro Leu Pro Gly Leu
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Leu Arg Arg Ala Tyr Ala Pro Leu Pro Gly Lys
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Leu Arg Arg Ala Tyr Ala Pro Leu Pro Asp Leu
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Trp Leu Arg Arg Ala Tyr Ala Pro Leu Pro Asp Lys
1               5                   10
```

```
<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Leu Arg Arg Ala Tyr Ala Pro Leu Pro Gly Leu Ser
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Leu Arg Arg Ala Tyr Ala Pro Leu Pro Gly Leu Thr
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Trp Leu Arg Arg Ala Tyr Ala Pro Leu Pro Gly Lys Ser
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Leu Arg Arg Ala Tyr Ala Pro Leu Pro Gly Lys Thr
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Trp Leu Arg Arg Ala Tyr Ala Pro Leu Pro Asp Leu Ser
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 141

Trp Leu Arg Arg Ala Tyr Ala Pro Leu Pro Asp Leu Thr
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Trp Leu Arg Arg Ala Tyr Ala Pro Leu Pro Asp Lys Ser
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Trp Leu Arg Arg Ala Tyr Ala Pro Leu Pro Asp Lys Thr
1               5                   10

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 144

Xaa Arg Arg Ala Ser Ala Pro Leu Pro
1               5

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 145

Xaa Leu Arg Arg Ala Ser Ala Pro Leu Pro
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: Phe, Tyr or Trp

<400> SEQUENCE: 146

Xaa Trp Leu Arg Arg Ala Ser Ala Pro Leu Pro
1               5                   10

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 147

Xaa Arg Arg Ala Thr Ala Pro Leu Pro
1               5

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 148

Xaa Leu Arg Arg Ala Thr Ala Pro Leu Pro
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 149

Xaa Trp Leu Arg Arg Ala Thr Ala Pro Leu Pro
1               5                   10

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 150

Xaa Arg Arg Ala Tyr Ala Pro Leu Pro
```

```
<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 151

Xaa Leu Arg Arg Ala Tyr Ala Pro Leu Pro
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 152

Xaa Trp Leu Arg Arg Ala Tyr Ala Pro Leu Pro
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 153

Xaa Arg Arg Ala Ser Ala Pro Leu Pro Gly
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 154

Xaa Arg Arg Ala Ser Ala Pro Leu Pro Asp
1               5                   10

<210> SEQ ID NO 155
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 155

Xaa Arg Arg Ala Ser Ala Pro Leu Pro Gly Leu
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 156

Xaa Arg Arg Ala Ser Ala Pro Leu Pro Gly Lys
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 157

Xaa Arg Arg Ala Ser Ala Pro Leu Pro Asp Leu
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 158

Xaa Arg Arg Ala Ser Ala Pro Leu Pro Asp Lys
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp
```

<400> SEQUENCE: 159

Xaa Arg Arg Ala Ser Ala Pro Leu Pro Gly Leu Ser
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 160

Xaa Arg Arg Ala Ser Ala Pro Leu Pro Gly Leu Thr
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 161

Xaa Arg Arg Ala Ser Ala Pro Leu Pro Gly Lys Ser
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 162

Xaa Arg Arg Ala Ser Ala Pro Leu Pro Gly Lys Thr
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 163

Xaa Arg Arg Ala Ser Ala Pro Leu Pro Asp Leu Ser
1               5                   10

```
<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 164

Xaa Arg Arg Ala Ser Ala Pro Leu Pro Asp Leu Thr
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 165

Xaa Arg Arg Ala Ser Ala Pro Leu Pro Asp Lys Ser
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 166

Xaa Arg Arg Ala Ser Ala Pro Leu Pro Asp Lys Thr
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 167

Xaa Leu Arg Arg Ala Ser Ala Pro Leu Pro Gly
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Phe, Tyr or Trp

<400> SEQUENCE: 168

Xaa Leu Arg Arg Ala Ser Ala Pro Leu Pro Asp
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 169

Xaa Leu Arg Arg Ala Ser Ala Pro Leu Pro Gly Leu
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 170

Xaa Leu Arg Arg Ala Ser Ala Pro Leu Pro Gly Lys
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 171

Xaa Leu Arg Arg Ala Ser Ala Pro Leu Pro Asp Leu
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 172
```

```
Xaa Leu Arg Arg Ala Ser Ala Pro Leu Pro Asp Lys
1               5                   10
```

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 173

```
Xaa Leu Arg Arg Ala Ser Ala Pro Leu Pro Gly Leu Ser
1               5                   10
```

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 174

```
Xaa Leu Arg Arg Ala Ser Ala Pro Leu Pro Gly Leu Thr
1               5                   10
```

<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 175

```
Xaa Leu Arg Arg Ala Ser Ala Pro Leu Pro Gly Lys Ser
1               5                   10
```

<210> SEQ ID NO 176
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 176

```
Xaa Leu Arg Arg Ala Ser Ala Pro Leu Pro Gly Lys Thr
1               5                   10
```

<210> SEQ ID NO 177
<211> LENGTH: 13
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 177

Xaa Leu Arg Arg Ala Ser Ala Pro Leu Pro Asp Leu Ser
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 178

Xaa Leu Arg Arg Ala Ser Ala Pro Leu Pro Asp Leu Thr
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 179

Xaa Leu Arg Arg Ala Ser Ala Pro Leu Pro Asp Lys Ser
1               5                   10

<210> SEQ ID NO 180
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 180

Xaa Leu Arg Arg Ala Ser Ala Pro Leu Pro Asp Lys Thr
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

<223> OTHER INFORMATION: Phe, Tyr or Trp

<400> SEQUENCE: 181

Xaa Trp Leu Arg Arg Ala Ser Ala Pro Leu Pro Gly
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 182

Xaa Trp Leu Arg Arg Ala Ser Ala Pro Leu Pro Asp
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 183

Xaa Trp Leu Arg Arg Ala Ser Ala Pro Leu Pro Gly Leu
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 184

Xaa Trp Leu Arg Arg Ala Ser Ala Pro Leu Pro Gly Lys
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 185

Xaa Trp Leu Arg Arg Ala Ser Ala Pro Leu Pro Asp Leu
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 186

Xaa Trp Leu Arg Arg Ala Ser Ala Pro Leu Pro Asp Lys
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 187

Xaa Trp Leu Arg Arg Ala Ser Ala Pro Leu Pro Gly Leu Ser
1               5                   10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 188

Xaa Trp Leu Arg Arg Ala Ser Ala Pro Leu Pro Gly Leu Thr
1               5                   10

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 189

Xaa Trp Leu Arg Arg Ala Ser Ala Pro Leu Pro Gly Lys Ser
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Phe, Tyr or Trp

<400> SEQUENCE: 190

Xaa Trp Leu Arg Arg Ala Ser Ala Pro Leu Pro Gly Lys Thr
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 191

Xaa Trp Leu Arg Arg Ala Ser Ala Pro Leu Pro Asp Leu Ser
1               5                   10

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 192

Xaa Trp Leu Arg Arg Ala Ser Ala Pro Leu Pro Asp Leu Thr
1               5                   10

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 193

Xaa Trp Leu Arg Arg Ala Ser Ala Pro Leu Pro Asp Lys Ser
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 194

Xaa Trp Leu Arg Arg Ala Ser Ala Pro Leu Pro Asp Lys Thr
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 195

Xaa Arg Arg Ala Thr Ala Pro Leu Pro Gly
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 196

Xaa Arg Arg Ala Thr Ala Pro Leu Pro Asp
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 197

Xaa Arg Arg Ala Thr Ala Pro Leu Pro Gly Leu
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 198

Xaa Arg Arg Ala Thr Ala Pro Leu Pro Gly Lys
1               5                   10

<210> SEQ ID NO 199
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 199

Xaa Arg Arg Ala Thr Ala Pro Leu Pro Asp Leu
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 200

Xaa Arg Arg Ala Thr Ala Pro Leu Pro Asp Lys
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 201

Xaa Arg Arg Ala Thr Ala Pro Leu Pro Gly Leu Ser
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 202

Xaa Arg Arg Ala Thr Ala Pro Leu Pro Gly Leu Thr
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Phe, Tyr or Trp

<400> SEQUENCE: 203

Xaa Arg Arg Ala Thr Ala Pro Leu Pro Gly Lys Ser
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 204

Xaa Arg Arg Ala Thr Ala Pro Leu Pro Gly Lys Thr
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 205

Xaa Arg Arg Ala Thr Ala Pro Leu Pro Asp Leu Ser
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 206

Xaa Arg Arg Ala Thr Ala Pro Leu Pro Asp Leu Thr
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 207

Xaa Arg Arg Ala Thr Ala Pro Leu Pro Asp Lys Ser
1               5                   10
```

```
<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 208

Xaa Arg Arg Ala Thr Ala Pro Leu Pro Asp Lys Thr
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 209

Xaa Leu Arg Arg Ala Thr Ala Pro Leu Pro Gly
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 210

Xaa Leu Arg Arg Ala Thr Ala Pro Leu Pro Asp
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 211

Xaa Leu Arg Arg Ala Thr Ala Pro Leu Pro Gly Leu
1               5                   10

<210> SEQ ID NO 212
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 212

Xaa Leu Arg Arg Ala Thr Ala Pro Leu Pro Gly Lys
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 213

Xaa Leu Arg Arg Ala Thr Ala Pro Leu Pro Asp Leu
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 214

Xaa Leu Arg Arg Ala Thr Ala Pro Leu Pro Asp Lys
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 215

Xaa Leu Arg Arg Ala Thr Ala Pro Leu Pro Gly Leu Ser
1               5                   10

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp
```

```
<400> SEQUENCE: 216

Xaa Leu Arg Arg Ala Thr Ala Pro Leu Pro Gly Leu Thr
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 217

Xaa Leu Arg Arg Ala Thr Ala Pro Leu Pro Gly Lys Ser
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 218

Xaa Leu Arg Arg Ala Thr Ala Pro Leu Pro Gly Lys Thr
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 219

Xaa Leu Arg Arg Ala Thr Ala Pro Leu Pro Asp Leu Ser
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 220

Xaa Leu Arg Arg Ala Thr Ala Pro Leu Pro Asp Leu Thr
1               5                   10

<210> SEQ ID NO 221
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 221

Xaa Leu Arg Arg Ala Thr Ala Pro Leu Pro Asp Lys Ser
1               5                   10

<210> SEQ ID NO 222
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 222

Xaa Leu Arg Arg Ala Thr Ala Pro Leu Pro Asp Lys Thr
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 223

Xaa Trp Leu Arg Arg Ala Thr Ala Pro Leu Pro Gly
1               5                   10

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 224

Xaa Trp Leu Arg Arg Ala Thr Ala Pro Leu Pro Asp
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Phe, Tyr or Trp

<400> SEQUENCE: 225

Xaa Trp Leu Arg Arg Ala Thr Ala Pro Leu Pro Gly Leu
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 226

Xaa Trp Leu Arg Arg Ala Thr Ala Pro Leu Pro Gly Lys
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 227

Xaa Trp Leu Arg Arg Ala Thr Ala Pro Leu Pro Asp Leu
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 228

Xaa Trp Leu Arg Arg Ala Thr Ala Pro Leu Pro Asp Lys
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 229

Xaa Trp Leu Arg Arg Ala Thr Ala Pro Leu Pro Gly Leu Ser
```

```
1               5                   10
```

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 230

```
Xaa Trp Leu Arg Arg Ala Thr Ala Pro Leu Pro Gly Leu Thr
1               5                   10
```

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 231

```
Xaa Trp Leu Arg Arg Ala Thr Ala Pro Leu Pro Gly Lys Ser
1               5                   10
```

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 232

```
Xaa Trp Leu Arg Arg Ala Thr Ala Pro Leu Pro Gly Lys Thr
1               5                   10
```

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 233

```
Xaa Trp Leu Arg Arg Ala Thr Ala Pro Leu Pro Asp Leu Ser
1               5                   10
```

<210> SEQ ID NO 234
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 234

Xaa Trp Leu Arg Arg Ala Thr Ala Pro Leu Pro Asp Leu Thr
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 235

Xaa Trp Leu Arg Arg Ala Thr Ala Pro Leu Pro Asp Lys Ser
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 236

Xaa Trp Leu Arg Arg Ala Thr Ala Pro Leu Pro Asp Lys Thr
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 237

Xaa Arg Arg Ala Tyr Ala Pro Leu Pro Gly
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp
```

<400> SEQUENCE: 238

Xaa Arg Arg Ala Tyr Ala Pro Leu Pro Asp
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 239

Xaa Arg Arg Ala Tyr Ala Pro Leu Pro Gly Leu
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 240

Xaa Arg Arg Ala Tyr Ala Pro Leu Pro Gly Lys
1               5                   10

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 241

Xaa Arg Arg Ala Tyr Ala Pro Leu Pro Asp Leu
1               5                   10

<210> SEQ ID NO 242
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 242

Xaa Arg Arg Ala Tyr Ala Pro Leu Pro Asp Lys
1               5                   10

```
<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 243

Xaa Arg Arg Ala Tyr Ala Pro Leu Pro Gly Leu Ser
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 244

Xaa Arg Arg Ala Tyr Ala Pro Leu Pro Gly Leu Thr
1               5                   10

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 245

Xaa Arg Arg Ala Tyr Ala Pro Leu Pro Gly Lys Ser
1               5                   10

<210> SEQ ID NO 246
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 246

Xaa Arg Arg Ala Tyr Ala Pro Leu Pro Gly Lys Thr
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Phe, Tyr or Trp

<400> SEQUENCE: 247

Xaa Arg Arg Ala Tyr Ala Pro Leu Pro Asp Leu Ser
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 248

Xaa Arg Arg Ala Tyr Ala Pro Leu Pro Asp Leu Thr
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 249

Xaa Arg Arg Ala Tyr Ala Pro Leu Pro Asp Lys Ser
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 250

Xaa Arg Arg Ala Tyr Ala Pro Leu Pro Asp Lys Thr
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 251
```

Xaa Leu Arg Arg Ala Tyr Ala Pro Leu Pro Gly
1               5                   10

<210> SEQ ID NO 252
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 252

Xaa Leu Arg Arg Ala Tyr Ala Pro Leu Pro Asp
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 253

Xaa Leu Arg Arg Ala Tyr Ala Pro Leu Pro Gly Leu
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 254

Xaa Leu Arg Arg Ala Tyr Ala Pro Leu Pro Gly Lys
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 255

Xaa Leu Arg Arg Ala Tyr Ala Pro Leu Pro Asp Leu
1               5                   10

<210> SEQ ID NO 256
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 256

Xaa Leu Arg Arg Ala Tyr Ala Pro Leu Pro Asp Lys
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 257

Xaa Leu Arg Arg Ala Tyr Ala Pro Leu Pro Gly Leu Ser
1               5                   10

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 258

Xaa Leu Arg Arg Ala Tyr Ala Pro Leu Pro Gly Leu Thr
1               5                   10

<210> SEQ ID NO 259
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 259

Xaa Leu Arg Arg Ala Tyr Ala Pro Leu Pro Gly Lys Ser
1               5                   10

<210> SEQ ID NO 260
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Phe, Tyr or Trp

<400> SEQUENCE: 260

Xaa Leu Arg Arg Ala Tyr Ala Pro Leu Pro Gly Lys Thr
1               5                   10

<210> SEQ ID NO 261
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 261

Xaa Leu Arg Arg Ala Tyr Ala Pro Leu Pro Asp Leu Ser
1               5                   10

<210> SEQ ID NO 262
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 262

Xaa Leu Arg Arg Ala Tyr Ala Pro Leu Pro Asp Leu Thr
1               5                   10

<210> SEQ ID NO 263
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 263

Xaa Leu Arg Arg Ala Tyr Ala Pro Leu Pro Asp Lys Ser
1               5                   10

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 264

Xaa Leu Arg Arg Ala Tyr Ala Pro Leu Pro Asp Lys Thr
1               5                   10
```

```
<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 265

Xaa Trp Leu Arg Arg Ala Tyr Ala Pro Leu Pro Gly
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 266

Xaa Trp Leu Arg Arg Ala Tyr Ala Pro Leu Pro Asp
1               5                   10

<210> SEQ ID NO 267
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 267

Xaa Trp Leu Arg Arg Ala Tyr Ala Pro Leu Pro Gly Leu
1               5                   10

<210> SEQ ID NO 268
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 268

Xaa Trp Leu Arg Arg Ala Tyr Ala Pro Leu Pro Gly Lys
1               5                   10

<210> SEQ ID NO 269
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: Phe, Tyr or Trp

<400> SEQUENCE: 269

Xaa Trp Leu Arg Arg Ala Tyr Ala Pro Leu Pro Asp Leu
1               5                   10

<210> SEQ ID NO 270
<211> LENGTH: 13
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Phe, Tyr or Trp

<400> SEQUENCE: 270

Xaa Trp Leu Arg Arg Ala Tyr Ala Pro Leu Pro Asp Lys
1               5                   10

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Phe, Tyr or Trp

<400> SEQUENCE: 271

Xaa Trp Leu Arg Arg Ala Tyr Ala Pro Leu Pro Gly Leu Ser
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Phe, Tyr or Trp

<400> SEQUENCE: 272

Xaa Trp Leu Arg Arg Ala Tyr Ala Pro Leu Pro Gly Leu Thr
1               5                   10

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Phe, Tyr or Trp

<400> SEQUENCE: 273
```

Xaa Trp Leu Arg Arg Ala Tyr Ala Pro Leu Pro Gly Lys Ser
1               5                   10

<210> SEQ ID NO 274
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 274

Xaa Trp Leu Arg Arg Ala Tyr Ala Pro Leu Pro Gly Lys Thr
1               5                   10

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 275

Xaa Trp Leu Arg Arg Ala Tyr Ala Pro Leu Pro Asp Leu Ser
1               5                   10

<210> SEQ ID NO 276
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 276

Xaa Trp Leu Arg Arg Ala Tyr Ala Pro Leu Pro Asp Leu Thr
1               5                   10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 277

Xaa Trp Leu Arg Arg Ala Tyr Ala Pro Leu Pro Asp Lys Ser
1               5                   10

<210> SEQ ID NO 278
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Tyr or Trp

<400> SEQUENCE: 278

Xaa Trp Leu Arg Arg Ala Tyr Ala Pro Leu Pro Asp Lys Thr
1               5                   10

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: This sequence may encompass 4-9 "Arg" residues

<400> SEQUENCE: 279

Arg Arg Arg Arg Arg Arg Arg Arg Arg
1               5

<210> SEQ ID NO 280
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gly Arg Lys Lys Arg Arg Gln Arg Arg Arg Pro Pro Gln
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Tyr Ala Arg Ala Ala Ala Arg Gln Ala Arg Ala
1               5                   10

<210> SEQ ID NO 282
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu
```

```
<210> SEQ ID NO 283
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Pro Leu Ser Ser Ile Phe Ser Arg Ile Gly Asp Pro
1               5                   10

<210> SEQ ID NO 285
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Ala Val Ala Leu Leu Pro Ala Val Leu Leu Ala Leu Leu Ala Pro
1               5                   10                  15

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Ala Val Leu Leu Pro Val Leu Leu Ala Ala Pro
1               5                   10

<210> SEQ ID NO 287
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Val Thr Val Leu Ala Leu Gly Ala Leu Ala Gly Val Gly Val Gly
1               5                   10                  15

<210> SEQ ID NO 288
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 288

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 289
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 290
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Lys Leu Ala Leu Lys Leu Ala Leu Lys Ala Leu Lys Ala Ala Leu Lys
1               5                   10                  15

Leu Ala

<210> SEQ ID NO 291
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Lys Ala Phe Ala Lys Leu Ala Ala Arg Leu Tyr Arg Lys Ala Gly Cys
1               5                   10                  15

<210> SEQ ID NO 293
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Lys Ala Phe Ala Lys Leu Ala Ala Arg Leu Tyr Arg Ala Ala Gly Cys
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Ala Phe Ala Lys Leu Ala Ala Arg Leu Tyr Arg Lys Ala Gly Cys
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Lys Ala Phe Ala Ala Leu Ala Ala Arg Leu Tyr Arg Lys Ala Gly Cys
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Lys Ala Phe Ala Lys Leu Ala Ala Gln Leu Tyr Arg Lys Ala Gly Cys
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Gly Gly Gly Tyr Gly Arg Lys Lys Arg Arg Gln Arg Arg Arg
1               5                   10                  15

<210> SEQ ID NO 298
<211> LENGTH: 160
<212> TYPE: PRT
<213> ORGANISM: Homo sapiens

<400> SEQUENCE: 298

Met Glu Ile Pro Val Pro Val Gln Pro Ser Trp Leu Arg Arg Ala Ser
1               5                   10                  15

Ala Pro Leu Pro Gly Leu Ser Ala Pro Gly Arg Leu Phe Asp Gln Arg
```

```
                 20                  25                  30

Phe Gly Glu Gly Leu Leu Glu Ala Glu Leu Ala Ala Leu Cys Pro Thr
             35                  40                  45

Thr Leu Ala Pro Tyr Tyr Leu Arg Ala Pro Ser Val Ala Leu Pro Val
         50                  55                  60

Ala Gln Val Pro Thr Asp Pro Gly His Phe Ser Val Leu Leu Asp Val
 65                  70                  75                  80

Lys His Phe Ser Pro Glu Glu Ile Ala Val Lys Val Val Gly Glu His
                 85                  90                  95

Val Glu Val His Ala Arg His Glu Arg Pro Asp Glu His Gly Phe
             100                 105                 110

Val Ala Arg Glu Phe His Arg Arg Tyr Arg Leu Pro Pro Gly Val Asp
             115                 120                 125

Pro Ala Ala Val Thr Ser Ala Leu Ser Pro Glu Gly Val Leu Ser Ile
         130                 135                 140

Gln Ala Ala Pro Ala Ser Ala Gln Ala Pro Pro Ala Ala Ala Lys
145                 150                 155                 160

<210> SEQ ID NO 299
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Tyr Gly Arg Lys Lys Arg Arg Gln Arg Arg Arg
1               5                   10

<210> SEQ ID NO 300
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phospho-Ser

<400> SEQUENCE: 300

Trp Leu Arg Arg Ala Ser Ala Pro Leu Pro Gly Leu
1               5                   10

<210> SEQ ID NO 301
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Phospho-Ser

<400> SEQUENCE: 301

Tyr Gly Arg Lys Lys Arg Arg Gln Arg Arg Arg Trp Leu Arg Arg Ala
1               5                   10                  15

Ser Ala Pro Leu Pro Gly Leu
            20
```

```
<210> SEQ ID NO 302
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phospho-Ser

<400> SEQUENCE: 302

Pro Arg Ser Leu Trp Ala Leu Gly Arg Pro Leu Ser Ala Lys
1               5                   10

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ser Trp Leu Arg Arg
1               5

<210> SEQ ID NO 304
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Leu Arg Arg
1

<210> SEQ ID NO 305
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Pro Ser Trp Leu Arg Arg
1               5

<210> SEQ ID NO 306
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Pro Ser Trp Leu Arg Arg
1               5

<210> SEQ ID NO 307
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 307

Val Gln Pro Ser Trp Leu Arg Arg
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Pro Val Gln Pro Ser Trp Leu Arg Arg
1               5

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Val Pro Val Gln Pro Ser Trp Leu Arg Arg
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Pro Val Pro Val Gln Pro Ser Trp Leu Arg Arg
1               5                   10

<210> SEQ ID NO 311
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ile Pro Val Pro Val Gln Pro Ser Trp Leu Arg Arg
1               5                   10

<210> SEQ ID NO 312
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Glu Ile Pro Val Pro Val Gln Pro Ser Trp Leu Arg Arg
1               5                   10
```

<210> SEQ ID NO 313
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Met Glu Ile Pro Val Pro Val Gln Pro Ser Trp Leu Arg Arg
1               5                   10

<210> SEQ ID NO 314
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Leu Ser Ala Pro
1               5

<210> SEQ ID NO 315
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Tyr Ala Arg Ala Ala Ala Arg Gln Ala Arg Ala Trp Leu Arg Arg Ala
1               5                   10                  15

Ser Ala Pro Leu Pro Gly Leu
            20

<210> SEQ ID NO 316
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass "Arg," "Arg Arg," SEQ
      ID NOS 1 or 303-313 and is 0 to 14 residues in length
<220> FEATURE:
<221> NAME/KEY: MOD_RES
<222> LOCATION: (16)..(16)
<223> OTHER INFORMATION: Ser, Thr, Tyr, Asp, Glu, hydroxylysine,
      hydroxyproline, phosphoserine analogs, and phosphotyrosine analogs
<220> FEATURE:
<221> NAME/KEY: MOD_RES
<222> LOCATION: (21)..(21)
<223> OTHER INFORMATION: Gly, Asp or not present
<220> FEATURE:
<221> NAME/KEY: MOD_RES
<222> LOCATION: (22)..(22)
<223> OTHER INFORMATION: Leu, Lys or not present
<220> FEATURE:
<221> NAME/KEY: MOD_RES
<222> LOCATION: (23)..(23)
<223> OTHER INFORMATION: Ser, Thr, Lys or not present
<220> FEATURE:
<221> NAME/KEY: misc_feature
<222> LOCATION: (21)..(160)
<223> OTHER INFORMATION: This region may encompass "Gly Leu Ser," "Gly Lys Ser," "Gly Leu Thr," "Gly Lys Thr," "Gly Leu Lys," "Gly Lys
Lys," "Asp Leu Ser," "Asp Lys Ser," "Asp Leu Thr," "Asp
Lys," "Asp Leu Lys," "Asp Lys Lys," or residues 21
<220> FEATURE:
<221> NAME/KEY: misc_feature
<222> LOCATION: (21)..(160)
<223> OTHER INFORMATION: continued from above; to 140 of SEQ ID NO: 298
     and is 0 to 140 residues in length; residues in this region may or
     may be present with the proviso that if it is not present,
     all residues C-term of that position are also not present
<220> FEATURE:
<223> OTHER INFORMATION: see specification as filed for detailed
     description of substitutions and preferred embodiments

<400> SEQUENCE: 316

Xaa Xaa Xaa Xaa Xaa Xaa Xaa Xaa Xaa Xaa Xaa Xaa Xaa Ala Xaa
1               5                   10                  15

Ala Pro Leu Pro Xaa Xaa Xaa Ala Pro Gly Arg Leu Phe Asp Gln Arg
            20              25                  30

Phe Gly Glu Gly Leu Leu Glu Ala Glu Leu Ala Ala Leu Cys Pro Thr
        35                  40                  45

Thr Leu Ala Pro Tyr Tyr Leu Arg Ala Pro Ser Val Ala Leu Pro Val
    50                  55                  60

Ala Gln Val Pro Thr Asp Pro Gly His Phe Ser Val Leu Leu Asp Val
65                  70                  75                  80

Lys His Phe Ser Pro Glu Glu Ile Ala Val Lys Val Val Gly Glu His
                85                  90                  95

Val Glu Val His Ala Arg His Glu Glu Arg Pro Asp Glu His Gly Phe
            100                 105                 110

Val Ala Arg Glu Phe His Arg Arg Tyr Arg Leu Pro Pro Gly Val Asp
            115                 120                 125

Pro Ala Ala Val Thr Ser Ala Leu Ser Pro Glu Gly Val Leu Ser Ile
        130                 135                 140

Gln Ala Ala Pro Ala Ser Ala Gln Ala Pro Pro Pro Ala Ala Ala Lys
145                 150                 155                 160

<210> SEQ ID NO 317
<211> LENGTH: 228
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: misc_feature
<222> LOCATION: (1)..(34)
<223> OTHER INFORMATION: This region may encompass any of SEQ ID NOS
     279-297 or 299 and is 4 to 34 residues in length or is absent
<220> FEATURE:
<221> NAME/KEY: MOD_RES
<222> LOCATION: (35)..(48)
<223> OTHER INFORMATION: This region may encompass "Arg," "Arg Arg," SEQ
     ID NOS 1 or 303-313 and is 0 to 14 residues in length
<220> FEATURE:
<221> NAME/KEY: MOD_RES
<222> LOCATION: (50)..(50)
<223> OTHER INFORMATION: Ser, Thr, Tyr, Asp, Glu, hydroxylysine,
     hydroxyproline, phosphoserine analogs, and phosphotyrosine analogs
<220> FEATURE:
<221> NAME/KEY: MOD_RES
<222> LOCATION: (55)..(55)
<223> OTHER INFORMATION: Gly, Asp or not present
<220> FEATURE:
<221> NAME/KEY: MOD_RES
<222> LOCATION: (56)..(56)
<223> OTHER INFORMATION: Leu, Lys or not present
<220> FEATURE:
<221> NAME/KEY: MOD_RES -continued

```
<222> LOCATION: (57)..(57)
<223> OTHER INFORMATION: Ser, Thr, Lys or not present
<220> FEATURE:
<221> NAME/KEY: misc_feature
<222> LOCATION: (55)..(194)
<223> OTHER INFORMATION: This region may encompass "Gly Leu Ser," "Gly
      Lys Ser," "Gly Leu Thr," "Gly Lys Thr," "Gly Leu Lys," "Gly Lys
      Lys," "Asp Leu Ser," "Asp Lys Ser," "Asp Leu Thr," "Asp
      Lys Thr," "Asp Leu Lys," "Asp Lys Lys," or residues 21
<220> FEATURE:
<221> NAME/KEY: misc_feature
<222> LOCATION: (55)..(194)
<223> OTHER INFORMATION: continued from above; to 140 of SEQ ID NO: 298
      and is 0 to 140 residues in length; residues in this region may or
      may not be present with the proviso that if it is not present, all
      residues C-term through position 194 are also not present
<220> FEATURE:
<221> NAME/KEY: MOD_RES
<222> LOCATION: (195)..(228)
<223> OTHER INFORMATION: This region may encompass SEQ ID NOS 279-297
      and 299 and is 4 to 34 residues in length or is absent
<220> FEATURE:
<223> OTHER INFORMATION: see specification as filed for detailed
      description of substitutions and preferred embodiments

<400> SEQUENCE: 317

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
                35                  40                  45

Ala Xaa Ala Pro Leu Pro Xaa Xaa Ala Pro Gly Arg Leu Phe Asp
 50                  55                  60

Gln Arg Phe Gly Glu Gly Leu Leu Glu Ala Glu Leu Ala Ala Cys
 65                  70                  75                  80

Pro Thr Thr Leu Ala Pro Tyr Tyr Leu Arg Ala Pro Ser Val Ala Leu
                 85                  90                  95

Pro Val Ala Gln Val Pro Thr Asp Pro Gly His Phe Ser Val Leu Leu
                100                 105                 110

Asp Val Lys His Phe Ser Pro Glu Glu Ile Ala Val Lys Val Val Gly
                115                 120                 125

Glu His Val Glu Val His Ala Arg His Glu Glu Arg Pro Asp Glu His
130                 135                 140

Gly Phe Val Ala Arg Glu Phe His Arg Arg Tyr Arg Leu Pro Pro Gly
145                 150                 155                 160

Val Asp Pro Ala Ala Val Thr Ser Ala Leu Ser Pro Glu Gly Val Leu
                165                 170                 175

Ser Ile Gln Ala Ala Pro Ala Ser Ala Gln Ala Pro Pro Ala Ala
                180                 185                 190

Ala Lys Xaa Xaa Xaa Xaa Xaa Xaa Xaa Xaa Xaa Xaa Xaa Xaa Xaa
                195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa
225

<210> SEQ ID NO 318
<211> LENGTH: 228
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: misc_feature
<222> LOCATION: (1)..(34)
<223> OTHER INFORMATION: This region may encompass any of SEQ ID NOS
      279-297 or 299 and is 4 to 34 residues in length or is absent
<220> FEATURE:
<221> NAME/KEY: MOD_RES
<222> LOCATION: (35)..(48)
<223> OTHER INFORMATION: This region may encompass "Arg," "Arg Arg," SEQ
      ID NOS 1 or 303-313 and is 0 to 14 residues in length
<220> FEATURE:
<221> NAME/KEY: MOD_RES
<222> LOCATION: (50)..(50)
<223> OTHER INFORMATION: Ser, Thr, Tyr, Asp, Glu, hydroxylysine,
      hydroxyproline, phosphoserine analogs, and phosphotyrosine analogs
<220> FEATURE:
<221> NAME/KEY: MOD_RES
<222> LOCATION: (55)..(55)
<223> OTHER INFORMATION: Gly, Asp or not present
<220> FEATURE:
<221> NAME/KEY: MOD_RES
<222> LOCATION: (56)..(56)
<223> OTHER INFORMATION: Leu, Lys or not present
<220> FEATURE:
<221> NAME/KEY: MOD_RES
<222> LOCATION: (57)..(57)
<223> OTHER INFORMATION: Ser, Thr, Lys or not present
<220> FEATURE:
<221> NAME/KEY: misc_feature
<222> LOCATION: (55)..(194)
<223> OTHER INFORMATION: This region may encompass "Gly Leu Ser," "Gly
      Lys Ser," "Gly Leu Thr," "Gly Lys Thr," "Gly Leu Lys," "Gly Lys
      Lys," "Asp Leu Ser," "Asp Lys Ser," "Asp Leu Thr," "Asp
      Lys Thr," "Asp Leu Lys," "Asp Lys Lys," or residues 21
<220> FEATURE:
<221> NAME/KEY: misc_feature
<222> LOCATION: (55)..(194)
<223> OTHER INFORMATION: continued from above; to 140 of SEQ ID NO: 298
      and is 0 to 140 residues in length; residues in this region may or
      may not be present with the proviso that if it is not present, all
      residues C-term through position 194 are also not present
<220> FEATURE:
<221> NAME/KEY: MOD_RES
<222> LOCATION: (195)..(228)
<223> OTHER INFORMATION: This region may encompass SEQ ID NOS 279-297
      and 299 and is 4 to 34 residues in length or is absent
<220> FEATURE:
<223> OTHER INFORMATION: see specification as filed for detailed
      description of substitutions and preferred embodiments

<400> SEQUENCE: 318

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Ala Xaa Ala Pro Leu Pro Xaa Xaa Xaa Ala Pro Gly Arg Leu Phe Asp
    50                  55                  60

Gln Arg Phe Gly Glu Gly Leu Leu Glu Ala Glu Leu Ala Ala Leu Cys
65                  70                  75                  80

Pro Thr Thr Leu Ala Pro Tyr Tyr Leu Arg Ala Pro Ser Val Ala Leu
                85                  90                  95

Pro Val Ala Gln Val Pro Thr Asp Pro Gly His Phe Ser Val Leu Leu
            100                 105                 110

Asp Val Lys His Phe Ser Pro Glu Glu Ile Ala Val Lys Val Val Gly
        115                 120                 125

Glu His Val Glu Val His Ala Arg His Glu Glu Arg Pro Asp Glu His
    130                 135                 140
```

```
Gly Phe Val Ala Arg Glu Phe His Arg Arg Tyr Arg Leu Pro Pro Gly
145                 150                 155                 160

Val Asp Pro Ala Ala Val Thr Ser Ala Leu Ser Pro Glu Gly Val Leu
                165                 170                 175

Ser Ile Gln Ala Ala Pro Ala Ser Ala Gln Ala Pro Pro Ala Ala
        180                 185                 190

Ala Lys Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa
    210                 215                 220

Xaa Xaa Xaa Xaa
225

<210> SEQ ID NO 319
<211> LENGTH: 11
<212> TYPE: PRT
<213> ORGANISM: Human immunodeficiency virus

<400> SEQUENCE: 319

Tyr Gly Arg Lys Lys Arg Arg Gln Arg Arg Arg
1               5                   10

<210> SEQ ID NO 320
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Phospho-Ser
<220> FEATURE:
<221> NAME/KEY: MOD_RES
<222> LOCATION: (24)..(24)
<223> OTHER INFORMATION: Ser, Thr, or Lys

<400> SEQUENCE: 320

Tyr Ala Arg Ala Ala Ala Arg Gln Ala Arg Ala Trp Leu Arg Arg Ala
1               5                   10                  15

Ser Ala Pro Leu Pro Gly Leu Xaa
            20

<210> SEQ ID NO 321
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Phospho-Ser

<400> SEQUENCE: 321

Tyr Ala Arg Ala Ala Ala Arg Gln Ala Arg Ala Trp Leu Arg Arg Ala
1               5                   10                  15

Ser Ala Pro Leu Pro Gly Leu Lys
            20
```

We claim:

1. A method for reducing scar formation, comprising administering to an individual in need thereof an amount effective to reduce scar formation of a polypeptide wherein the polypeptide sequence is:

B1-X1-A(X2)APLP—X3-B2 wherein X1 is the amino acids of the sequence WLRR (SEQ ID NO: 1);
X2 is S and is phosphorylated;
X3 is Z1-Z2-Z3, wherein Z1 is G;
Z2 is L;
Z3 is selected from the group consisting of S, T, and K; and
wherein B1 is a transduction domain and B2 is absent or comprises a transduction domain.

2. The method of claim 1 wherein one or both of B1 and B2 each independently comprises the amino acid sequence of SEQ ID NO: 299 or SEQ ID NO: 281.

3. The method of claim 1, wherein B2 is absent.

4. The method of claim 1 wherein the individual in need thereof has a wound selected from the group consisting of lacerations; burns; punctures; pressure sores; bed sores; canker sores; trauma, bites; fistulas; ulcers; lesions caused by infections; periodontal wounds; endodontic wounds; burning mouth syndrome; laparotomy wounds; surgical wounds; incisional wounds; contractures after burns; tissue fibrosis; and wounds resulting from cosmetic surgical procedures.

5. The method of claim 1 wherein the method is used for reducing initial scar formation.

6. A method for promoting wound healing, comprising administering to an individual in need thereof an amount effective to promote wound healing of a polypeptide wherein the polypeptide sequence is:

B1-X1-A(X2)APLP—X3-B2 wherein X1 is the amino acids of the sequence WLRR (SEQ ID NO: 1);
X2 is S and is phosphorylated;
X3 is Z1-Z2-Z3, wherein Z1 is G;
Z2 is L;
Z3 is selected from the group consisting of S, T, and K; and
wherein B1 is a transduction domain and B2 is absent or comprises a transduction domain.

7. The method of claim 6 wherein one or both of B1 and B2 each independently comprises the amino acid sequence of SEQ ID NO: 299 or SEQ ID NO: 281.

8. The method of claim 6, wherein B2 is absent.

9. The method of claim 6 wherein the individual in need thereof has a wound selected from the group consisting of lacerations; burns; punctures; pressure sores; bed sores; canker sores; trauma, bites; fistulas; ulcers; lesions caused by infections; periodontal wounds; endodontic wounds; burning mouth syndrome; laparotomy wounds; surgical wounds; incisional wounds; contractures after burns; tissue fibrosis; and wounds resulting from cosmetic surgical procedures.

* * * * *